US010660450B2

United States Patent
Harada et al.

(10) Patent No.: US 10,660,450 B2
(45) Date of Patent: May 26, 2020

(54) AIR-CONDITIONING CONTROL METHOD AND AIR-CONDITIONING CONTROL SYSTEM FOR IN-BED AIR CONDITIONING

(71) Applicant: Panasonic Intellectual Property Management Co., Ltd., Osaka (JP)

(72) Inventors: Masaaki Harada, Osaka (JP); Tomohiko Kitamura, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 97 days.

(21) Appl. No.: 15/906,358

(22) Filed: Feb. 27, 2018

(65) Prior Publication Data

US 2018/0271299 A1   Sep. 27, 2018

(30) Foreign Application Priority Data

Mar. 22, 2017  (JP) .................................. 2017-055350
Nov. 1, 2017   (JP) .................................. 2017-211665

(51) Int. Cl.
*A47C 21/04*   (2006.01)
*F24F 1/00*    (2019.01)
(Continued)

(52) U.S. Cl.
CPC .......... *A47C 21/044* (2013.01); *A47C 21/048* (2013.01); *A47C 31/008* (2013.01); *A61B 5/11* (2013.01); *A61B 5/1113* (2013.01); *A61B 5/4809* (2013.01); *A61B 5/6892* (2013.01); *F24F 1/00* (2013.01); *F24F 1/0007* (2013.01); *F24F 11/79* (2018.01); *A61B 5/024* (2013.01); *A61B 5/0816* (2013.01);
(Continued)

(58) Field of Classification Search
CPC ..... A47C 21/044; F24F 11/79; F24F 2110/10; F24F 2110/20; F24F 2120/12; F24F 2120/14; F24F 2221/10
See application file for complete search history.

(56) References Cited

U.S. PATENT DOCUMENTS 5,299,428 A    4/1994   Kawaguri et al.
7,809,472 B1 * 10/2010  Silva ........................ F24F 3/065
                                                    700/277

(Continued)

FOREIGN PATENT DOCUMENTS

JP    5-288387      11/1993
JP    2009-183354   8/2009
JP    2009-247846   10/2009

*Primary Examiner* — Jonathan Bradford
(74) *Attorney, Agent, or Firm* — Greenblum & Bernstein, P.L.C.

(57) ABSTRACT

An air-conditioning control system includes an in-bed air conditioner which adjusts an in-bed temperature using air in a room interior, an in-room air conditioner which adjusts an in-room temperature, an in-bed environment measurer which measures the in-bed temperature, an in-room environment measurer which measures the in-room temperature, and an air-conditioning controller which performs first cooperation control that controls operation of the in-bed air conditioner and a wind direction of the in-room air conditioner on the basis of the in-bed temperature acquired from the in-bed environment measurer and the in-room temperature acquired from the in-room environment measurer.

17 Claims, 8 Drawing Sheets

(51) Int. Cl.
  *A61B 5/00*      (2006.01)
  *A61B 5/11*      (2006.01)
  *A47C 31/00*     (2006.01)
  *F24F 11/79*     (2018.01)
  *F24F 1/0007*    (2019.01)
  *F24F 120/12*    (2018.01)
  *F24F 1/0071*    (2019.01)
  *F24F 11/65*     (2018.01)
  *F24F 110/10*    (2018.01)
  *A61B 5/08*      (2006.01)
  *A61B 5/024*     (2006.01)
  *A61M 21/00*     (2006.01)

(52) U.S. Cl.
  CPC .... *A61B 5/1102* (2013.01); *A61M 2021/0066* (2013.01); *A61M 2205/3372* (2013.01); *A61M 2205/3561* (2013.01); *F24F 1/0071* (2019.02); *F24F 11/65* (2018.01); *F24F 2110/10* (2018.01); *F24F 2120/12* (2018.01); *F24F 2221/10* (2013.01)

(56) References Cited

U.S. PATENT DOCUMENTS 8,768,520 B2 *  7/2014  Oexman ............. A47C 27/061
                                              700/276
2015/0320588 A1 * 11/2015  Connor ................ A61F 7/0097
                                              607/107

* cited by examiner

AIR-CONDITIONING CONTROL METHOD AND AIR-CONDITIONING CONTROL SYSTEM FOR IN-BED AIR CONDITIONING

BACKGROUND

1. Technical Field

The present disclosure relates to an air-conditioning control method and an air-conditioning control system for in-bed air conditioning and, more particularly, to an air-conditioning control method and an air-conditioning control system for making a bed interior comfortable by performing collaborative control of an in-room air conditioner and an in-bed air conditioner.

2. Description of the Related Art

Sleep is said to occupy one-third of a human lifetime. To improve the quality of sleep, an apparatus for making a bed interior an environment more suitable for sleep is disclosed. For example, Japanese Unexamined Patent Application Publication No. 5-288387 discloses a bedroom temperature and humidity control apparatus which estimates a thermal sensation and a perspiratory sensation on the basis of an in-bed temperature and humidity and controls an in-room temperature and humidity.

Japanese Unexamined Patent Application Publication No. 2009-247846 discloses an in-bed temperature management apparatus which measures a heart rate during sleep to judge the depth of sleep, adjusts an in-bed temperature in accordance with the depth of sleep, and simultaneously adjusts an in-room temperature if the room temperature is significantly low or high.

Japanese Unexamined Patent Application Publication No. 2009-183354 discloses air circulation type bedding which prevents a bed interior from becoming hot and humid by circulating air whose temperature is lower than a body surface temperature through a mattress.

SUMMARY

However, the above-described bedroom temperature and humidity control apparatus or the like cannot always perform in-bed air conditioning comfortable for a person and requires further improvement.

In one general aspect, the techniques disclosed here feature an air-conditioning control method for cooperatively controlling (i) an in-bed air conditioner which adjusts an in-bed temperature using air in a room interior and (ii) an in-room air conditioner which adjusts an in-room temperature, using a processor, the air-conditioning control method including acquiring the in-bed temperature from an in-bed environment measurer, acquiring the in-room temperature from an in-room environment measurer, and performing first cooperation control that controls operation of the in-bed air conditioner and a wind direction of the in-room air conditioner on the basis of the acquired in-bed temperature and the acquired in-room temperature.

These general and specific aspects may be implemented using a system, a method, and a computer program, and any combination of systems, methods, and computer programs.

The above-described aspect allows steadier implementation of in-bed air conditioning comfortable for a person.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1:
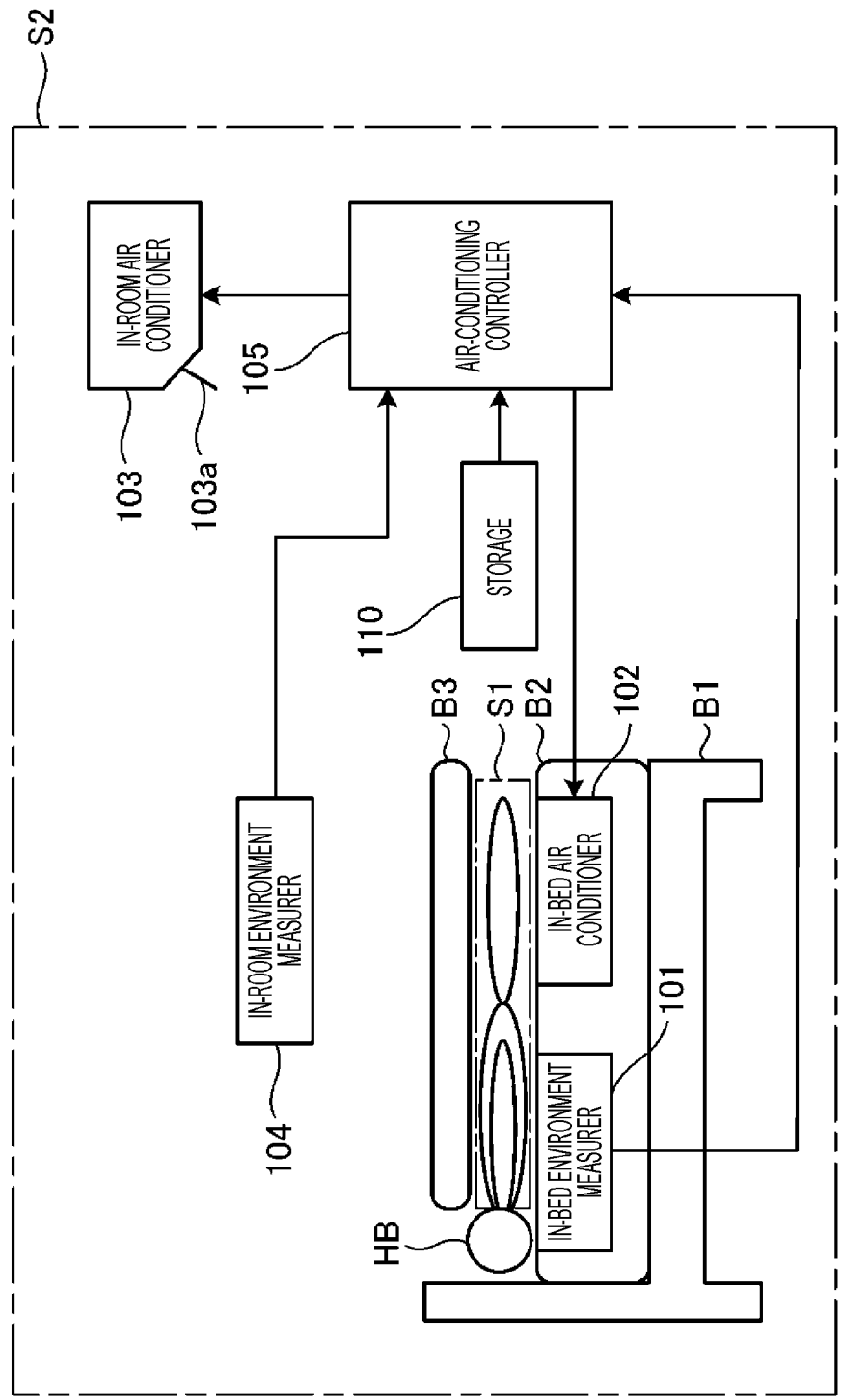
FIG. 1 is a diagram showing an example of the configuration of an air-conditioning control system according to a first embodiment of the present disclosure.

Underlying Knowledge Forming Basis of the Present Disclosure

The above-described bedroom temperature and humidity control apparatus disclosed in Japanese Unexamined Patent Application Publication No. 05-288387 aims to improve an in-bed environment by adjusting an in-room temperature and humidity on the basis of an in-bed temperature and humidity but suffers from the problem of the inability to make a bed interior comfortable as intended and implement effective in-bed air conditioning in a short time period, depending on bedding to be used.

The in-bed temperature management apparatus disclosed in Japanese Unexamined Patent Application Publication No. 2009-247846 uses temperature-adjusted liquid or air to adjust an in-bed temperature and suffers from the problem of the need for a heat source and a cooling source for in-bed air conditioning only and expensiveness of an apparatus price. Additionally, since an in-room temperature is adjusted only if the room temperature is significantly low or high, effective in-bed air conditioning cannot be implemented in a short time period if the room temperature is slightly low or high.

The air circulation type bedding disclosed in Japanese Unexamined Patent Application Publication No. 2009-183354 aims to make a bed interior comfortable by taking air around bedding into the bed interior but suffers from the problem of the inability to obtain expected effects and implement effective in-bed air conditioning in a short time period, depending on the situation of an in-room environment around the bedding.

The present inventors have made an earnest study on how to utilize an in-room air conditioner, such as an air conditioner, to implement effective in-bed air conditioning in a short time period. As a result, the present inventors have devised an air-conditioning control method and an air-conditioning control system for making a bed interior comfortable by performing collaborative control of an in-room air conditioner and an in-bed air conditioner and have completed the present disclosure.

An air-conditioning control method according to an aspect of the present disclosure is a method for cooperatively controlling (i) an in-bed air conditioner which adjusts an in-bed temperature using air in a room interior and (ii) an in-room air conditioner which adjusts an in-room temperature, using a processor, the method including acquiring the in-bed temperature from an in-bed environment measurer, acquiring the in-room temperature from an in-room environment measurer, and performing first cooperation control that controls operation of the in-bed air conditioner and a wind direction of the in-room air conditioner on the basis of the acquired in-bed temperature and the acquired in-room temperature.

With the above-described configuration, the in-bed temperature is acquired from the in-bed environment measurer, the in-room temperature is acquired from the in-room environment measurer, and the first cooperation control that controls the operation of the in-bed air conditioner and the wind direction of the in-room air conditioner is performed on the basis of the acquired in-bed temperature and the acquired in-room temperature. It is thus possible to adjust the in-bed temperature using the temperature-adjusted air in the room interior and more steadily implement in-bed air conditioning comfortable for a person.

The air-conditioning control method may further include acquiring a target in-bed temperature and a target in-room temperature from a storage, and the first cooperation control may be second cooperation control that calculates (i) an in-bed temperature difference which is a difference between the in-bed temperature and the target in-bed temperature and (ii) an in-room temperature difference which is a difference between the in-room temperature and the target in-room temperature, and controls the operation of the in-bed air conditioner and the wind direction of the in-room air conditioner on the basis of the in-bed temperature difference and the in-room temperature difference.

With the above-described configuration, the target in-bed temperature and the target in-room temperature are acquired from the storage, the in-bed temperature difference that is the difference between the in-bed temperature and the target in-bed temperature and the in-room temperature difference that is the difference between the in-room temperature and the target in-room temperature are calculated, and the operation of the in-bed air conditioner and the wind direction of the in-room air conditioner are controlled on the basis of the in-bed temperature difference and the in-room temperature difference. It is thus possible to more steadily implement in-bed air conditioning comfortable for a person in accordance with the in-bed temperature difference and the in-room temperature difference.

The second cooperation control may include activating the in-bed air conditioner and setting the wind direction of the in-room air conditioner to a bed direction if the in-bed temperature difference is larger than the in-room temperature difference.

With the above-described configuration, if the in-bed temperature difference is larger than the in-room temperature difference, the in-bed air conditioner is brought into operation, and the wind direction of the in-room air conditioner is set to the bed direction. It is thus possible to efficiently supply the temperature-adjusted air in the room interior to the in-bed air conditioner and implement effective in-bed air conditioning in a shorter time period.

The air-conditioning control method may further include acquiring information on an action of a person in the room interior from a biological information measurer or a terminal owned by the person, and the second cooperation control may be third cooperation control that controls the operation of the in-bed air conditioner and the wind direction of the in-room air conditioner on the basis of a relation between the in-bed temperature difference and a first threshold, a relation between the in-room temperature difference and a second threshold, and the acquired information on the action of the person.

With the above-described configuration, the operation of the in-bed air conditioner and the wind direction of the in-room air conditioner are controlled on the basis of the relation between the in-bed temperature difference and the first threshold, the relation between the in-room temperature difference and the second threshold, and the information on the action of the person. It is thus possible to give priority to comfort of the person active in the room interior or effectively make a bed interior comfortable, in accordance with the action of the person.

The third cooperation control may include controlling the wind direction of the in-room air conditioner such that the wind direction is a direction for in-room air conditioning if the in-bed temperature difference is not less than the first threshold, the in-room temperature difference is not less than the second threshold, and the acquired information on the action of the person indicates that the person is active, and activating the in-bed air conditioner and setting the wind direction of the in-room air conditioner to a bed direction if the in-room temperature difference acquired after the controlling is less than the second threshold.

With the above-described configuration, if the in-bed temperature difference is not less than the first threshold, the in-room temperature difference is not less than the second threshold, and the acquired information on the action of the person indicates that the person is active, the wind direction of the in-room air conditioner is controlled so as to be the direction for in-room air conditioning. It is thus possible to give priority to comfort of the person active in the room interior. If the in-room temperature difference acquired after the controlling is less than the second threshold, the in-bed air conditioner is brought into operation, and the wind direction of the in-room air conditioner is set to the bed direction. Since air in the room interior which is air to be fed into the bed interior is comfortable, the bed interior can be efficiently made comfortable.

The third cooperation control may include controlling the wind direction of the in-room air conditioner such that the wind direction is a direction for in-room air conditioning if the in-bed temperature difference is not less than the first threshold, the in-room temperature difference is not less than the second threshold, and the acquired information on the action of the person indicates that the person is active, and activating the in-bed air conditioner and setting the wind direction of the in-room air conditioner to a bed direction if the information on the action of the person acquired after the controlling indicates that the person is about to sleep or is asleep.

With the above-described configuration, if the in-bed temperature difference is not less than the first threshold, the in-room temperature difference is not less than the second threshold, and the acquired information on the action of the person indicates that the person is active, the wind direction of the in-room air conditioner is controlled so as to be the direction for in-room air conditioning. It is thus possible to give priority to comfort of the person active in the room interior. If the information on the action of the person acquired after the controlling indicates that the person is about to sleep or is asleep, the in-bed air conditioner is brought into operation, and the wind direction of the in-room air conditioner is set to the bed direction. Even if the room interior is not comfortable, sleep of the person that is about to sleep or is asleep can be made comfortable by giving priority to in-bed air conditioning.

The first cooperation control may include activating the in-bed air conditioner and setting the wind direction of the in-room air conditioner to a bed direction if the in-room temperature is closer to the target in-bed temperature than the in-bed temperature.

With the above-described configuration, if the in-room temperature is closer to the target in-bed temperature than the in-bed temperature, the in-bed air conditioner is brought into operation, and the wind direction of the in-room air conditioner is set to the bed direction. It is thus possible to adjust the in-bed temperature using air in the room interior, the air whose temperature is close to the target in-bed temperature suitable for sleep, and implement effective in-bed air conditioning in a shorter time period.

The air-conditioning control method may further include acquiring an in-bed humidity from the in-bed environment measurer, acquiring an in-room humidity from the in-room environment measurer, and acquiring a target in-bed comfort level and a target in-room comfort level from the storage, and the first cooperation control may be fourth cooperation control that calculates an in-bed comfort level which serves as a barometer for in-bed comfort using the in-bed temperature and the in-bed humidity and calculates an in-bed comfort level difference which is a difference between the in-bed comfort level and the target in-bed comfort level, calculates an in-room comfort level which serves as a barometer for in-room comfort using the in-room temperature and the in-room humidity and calculates an in-room comfort level difference which is a difference between the in-room comfort level and the target in-room comfort level, and controls the operation of the in-bed air conditioner and the wind direction of the in-room air conditioner on the basis of the in-bed comfort level difference and the in-room comfort level difference.

With the above-described configuration, the in-bed humidity, the in-room humidity, the target in-bed comfort level, and the target in-room comfort level are acquired in addition to the in-bed temperature and the in-room temperature, the in-bed comfort level serving as a barometer for in-bed comfort is calculated using the acquired in-bed temperature and in-bed humidity, the in-bed comfort level difference that is the difference between the calculated current in-bed comfort level and the target in-bed comfort level suitable for sleep is calculated, the in-room comfort level serving as a barometer for in-room comfort is calculated using the acquired in-room temperature and in-room humidity, the in-room comfort level difference that is the difference between the calculated current in-room comfort level and the target in-room comfort level suitable for sleep is calculated, and the operation of the in-bed air conditioner and the wind direction of the in-room air conditioner are controlled on the basis of the in-bed comfort level difference and the in-room comfort level difference. If the in-bed comfort level difference is larger than the in-room comfort level difference, the in-bed air conditioner is brought into operation to adjust the in-bed temperature, and priority is given to the bed interior with a larger difference from a target comfort level. It is thus possible to adjust the in-bed temperature and make the bed interior more comfortable in a shorter time period.

The air-conditioning control method may further include acquiring biological information of a person from a biological information measurer, and judging a sleep-related state of the person on the basis of the biological information, and in the first cooperation control, at least one of the operation of the in-bed air conditioner and a setup temperature of the in-room air conditioner may be controlled on the basis of the in-bed temperature, the in-room temperature, and the sleep-related state.

With the above-described configuration, the biological information of the person is acquired, the sleep-related state of the person is judged on the basis of the acquired biological information, and at least one of the operation of the in-bed air conditioner and the setup temperature of the in-room air conditioner is controlled on the basis of the current in-bed temperature and in-room temperature and the current sleep-related state. It is thus possible to adjust the in-bed temperature using air in the room interior temperature-adjusted in accordance with the sleep-related state of the person and implement in-bed air conditioning suitable for the sleep-related state of the person.

In the first cooperation control, the in-bed air conditioner may be activated if the state is a sleeping state.

With the above-described configuration, if the current state is the sleeping state, the in-bed air conditioner is brought into operation to adjust the in-bed temperature. It is thus possible to adjust the in-bed temperature to a temperature suitable for sleep and implement in-bed air conditioning suitable for sleep.

In the first cooperation control, the in-bed air conditioner may be activated if the state is a waking state.

With the above-described configuration, if the current state is the waking state, the in-bed air conditioner is brought into operation to dry the bed interior. It is thus possible to dry bedding with moisture absorbed during sleep.

If the state shifts to a sleeping state in the first cooperation control, the setup temperature of the in-room air conditioner may be raised with the in-bed air conditioner kept operating when the in-room air conditioner is in cooling or dehumidification operation, and the in-bed air conditioner may be brought out of operation and the setup temperature of the in-room air conditioner may be lowered when the in-room air conditioner is in heating operation.

With the above-described configuration, if the current state shifts to the sleeping state, the setup temperature of the in-room air conditioner is raised with the in-bed air conditioner kept operating when the in-room air conditioner is in cooling or dehumidification operation, and the in-bed air conditioner is brought out of operation and the setup temperature of the in-room air conditioner is lowered when the in-room air conditioner is in heating operation. It is thus possible to adjust the in-room temperature to a temperature suitable for sleep in accordance with an operation mode of the in-room air conditioner and adjust the in-bed temperature to a temperature suitable for sleep.

If the state is a state having a light sleep before rising in the first cooperation control, the setup temperature of the in-room air conditioner may be raised with the in-bed air conditioner kept operating when the in-room air conditioner is in cooling or dehumidification operation, and the setup temperature of the in-room air conditioner may be raised when the in-room air conditioner is in heating operation.

With the above-described configuration, if the current state is the state having a light sleep before rising, the setup temperature of the in-room air conditioner is raised with the in-bed air conditioner kept operating when the in-room air conditioner is in cooling or dehumidification operation, and the setup temperature of the in-room air conditioner is raised when the in-room air conditioner is in heating operation. It is thus possible to adjust a temperature of an in-room space to an environmental temperature, at which the person after rising can easily perform activity, in a state in which the in-bed temperature is maintained at a temperature suitable for sleep.

The biological information may include body motion data which represents motion of the person during sleep, and the judging the state may include judging the state from the body motion data and the in-bed temperature, and the setup temperature of the in-room air conditioner may be lowered with the in-bed air conditioner kept operating if the state is a state having difficulty in sleeping well in the first cooperation control.

With the above-described configuration, the body motion data that represents the motion of the person during sleep is acquired, the sleep-related state of the person is judged from the acquired body motion data and the in-bed temperature, and the setup temperature of the in-room air conditioner is lowered with the in-bed air conditioner kept operating if the current state is the state having difficulty in sleeping well. It is thus possible to lower the in-room temperature to a temperature suitable for sleep and lower the in-bed temperature using air in the room interior at the lowered temperature, and to implement in-bed air conditioning suitable for sleep even if the person has difficulty in sleeping well.

The air-conditioning control method may further include acquiring an action schedule from an action schedule manager which manages the action schedule of the person, and in the first cooperation control, the in-bed air conditioner may be brought into operation a predetermined time period before a bedtime indicated by the action schedule.

With the above-described configuration, the action schedule is acquired from the action schedule manager that manages the action schedule of the person, and the in-bed air conditioner is brought into operation to adjust the in-bed temperature the predetermined time period before the bedtime indicated by the action schedule. It is thus possible to automatically adjust the in-bed temperature to a temperature suitable for sleep by the bedtime.

The in-room air conditioner may have a first outlet and a second outlet, and in the first cooperation control, a wind direction of at least one of the first outlet and the second outlet may be controlled so as to be a bed direction.

With the above-described configuration, the wind direction of the one of the first and second outlets of the in-room air conditioner is controlled so as to be the bed direction. It is thus possible to efficiently supply temperature-adjusted air from one of the outlets to the in-bed air conditioner and efficiently supply temperature-adjusted air from the other outlet to the room interior. At the time of controlling the wind direction of the one of the first and second outlets of the in-room air conditioner such that the wind direction is the bed direction, the wind direction is desirably controlled so as to face a direction of an air suction port of the in-bed air conditioner.

The air-conditioning control method may further include setting a ratio between a bed direction and a direction other than the bed direction in the wind direction of the in-room air conditioner in accordance with a ratio between the in-bed temperature difference and the in-room temperature difference in the second cooperation control.

With the above-described configuration, the ratio between the bed direction and the direction other than the bed direction in the wind direction of the in-room air conditioner is set in accordance with the ratio between the in-bed temperature difference and the in-room temperature difference. It is possible to preferentially air-condition one with a higher degree of discomfort of the bed interior and the room interior while air-conditioning the bed interior and the whole of the room interior. The other can thus be inhibited from falling into an uncomfortable state at the time of air-conditioning only one of the bed interior and the room interior.

The present disclosure can be implemented not only as an air-conditioning control method for executing the above-described characteristic processes but also as an air-conditioning control system or the like including a characteristic configuration which supports the characteristic processes to be executed by the air-conditioning control method. Thus, same effects as those of the above-described air-conditioning control method can be produced by the different aspect below.

An air-conditioning control system according to another aspect of the present disclosure includes an in-bed air conditioner which adjusts an in-bed temperature using air in a room interior, an in-room air conditioner which adjusts an in-room temperature, an in-bed environment measurer which measures the in-bed temperature, an in-room environment measurer which measures the in-room temperature, and a controller which performs first cooperation control that controls operation of the in-bed air conditioner and a wind direction of the in-room air conditioner on the basis of the in-bed temperature acquired from the in-bed environment measurer and the in-room temperature acquired from the in-room environment measurer.

Embodiments of the present disclosure will be described below with reference to the drawings. Note that the embodiments described below are comprehensive or specific examples. Numerical values, shapes, constituent elements, steps, the order of steps, and the like illustrated in the embodiments are merely illustrative and are not intended to limit the present disclosure. Additionally, among constituent elements in the embodiments, those not set forth in the independent claims indicating the top level concept will be described as optical constituent elements. In addition, matters in all the embodiments may be arbitrarily combined.

First Embodiment

FIG. 1 is a diagram showing an example of the configuration of an air-conditioning control system according to a first embodiment of the present disclosure. The air-conditioning control system shown in FIG. 1 includes an in-bed environment measurer 101, an in-bed air conditioner 102, an in-room air conditioner 103, an in-room environment measurer 104, an air-conditioning controller 105, and a storage 110.

As shown in FIG. 1, for example, a bed B1 is installed in a room where a user HB sleeps, a mattress B2 is laid on the bed B1, and a comforter B3 is laid on the mattress B2. The user HB sleeps using the mattress B2 and the comforter B3.

The air-conditioning control system according to the present embodiment divides the room where the user HB sleeps into two spaces and measures an environmental state. One space is an in-bed space S1 which is a space between the comforter B3 and the mattress B2, and the other space is an in-room space S2 which covers an entire room interior except the in-bed space S1.

The in-bed environment measurer 101 is composed of a temperature sensor or the like and is attached to a predetermined position in the mattress B2, for example, the vicinity of an upper body of the user HB. The in-bed environment measurer 101 measures a temperature (an in-bed temperature) of the in-bed space S1 and outputs the temperature of the in-bed space S1 to the air-conditioning controller 105.

The in-room environment measurer 104 is composed of a temperature sensor or the like and is attached to a predetermined position in the in-room space S2, for example, a middle position in the in-room space S2. The in-room environment measurer 104 measures a temperature (an in-room temperature) of the in-room space S2 and outputs the temperature of the in-room space S2 to the air-conditioning controller 105.

Note that the configuration of the in-bed environment measurer 101 is not particularly limited to the above-described example and that the in-bed environment measurer 101 may be, for example, installed in the comforter B3 or at the bed B1 instead of being installed in the mattress B2. The number of in-bed environment measurers 101 is not limited to one, and a plurality of in-bed environment measurers 101 may be installed. The configuration of the in-room environment measurer 104 is not particularly limited to the above-described example, and the in-room environment measurer 104 may be provided, for example, inside the in-room air conditioner 103 or in the vicinity of a head of the bed B1.

The in-room air conditioner 103 is composed of, for example, an air conditioner and is attached to an upper portion of one of walls forming the in-room space S2. The in-room air conditioner 103 can perform cooling operation, heating operation, and dehumidification operation and adjusts the temperature of the in-room space S2 in accordance with an operating state, a setup temperature, and the like. The in-room air conditioner 103 includes an outlet (louver) 103a and can change a wind direction.

The in-bed air conditioner 102 is incorporated in, for example, the mattress B2, is composed of an in-bed ventilation device which ventilates the in-bed space S1 using air in the in-room space S2, and adjusts the temperature of the in-bed space S1 using the air in the in-room space S2. For example, the in-bed air conditioner 102 cools the in-bed space S1 filled with heated air and adjusts the in-bed temperature by taking air in the vicinity of the mattress B2 which is temperature-adjusted by the in-room air conditioner 103 into the in-bed space S1.

Figure 2:
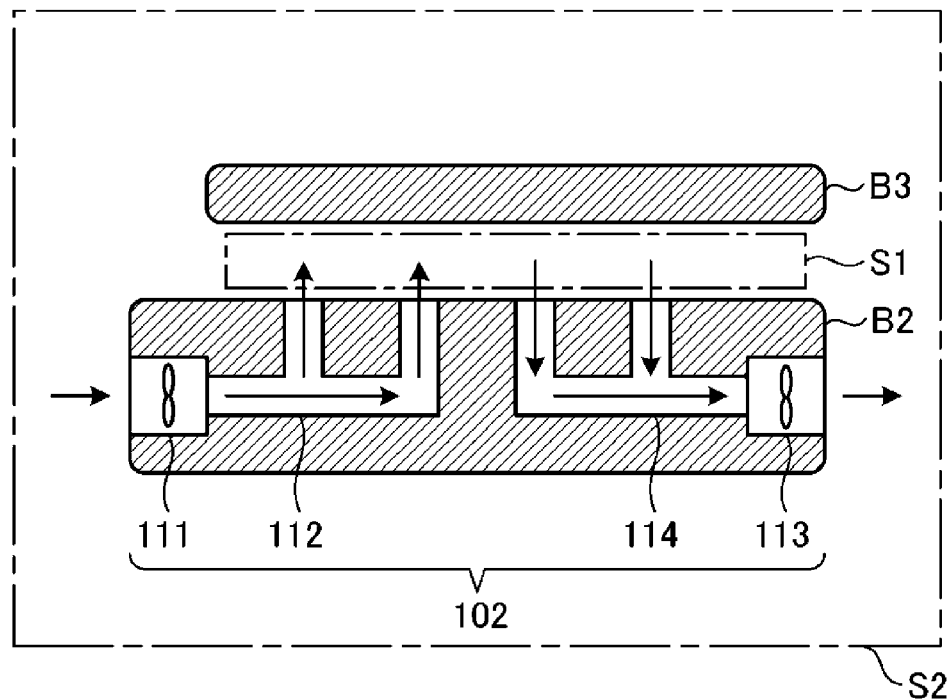
FIG. 2 is a schematic cross-sectional view showing an example of the configuration of an in-bed air conditioner shown in FIG. 1.

FIG. 2 is a schematic cross-sectional view showing an example of the configuration of the in-bed air conditioner 102 shown in FIG. 1. As shown in FIG. 2, the in-bed air conditioner 102 includes ventilators 111 and 113 and air passages 112 and 114.

The ventilator 111 is fixed to a head side of the mattress B2 while communicating with the in-room space S2 and the air passage 112. The air passage 112 has a plurality of air vents which communicate with the in-bed space S1. Similarly, the ventilator 113 is fixed to a foot side of the mattress B2 while communicating with the in-room space S2 and the air passage 114. The air passage 114 has a plurality of air vents which communicate with the in-bed space S1. The ventilators 111 and 113 are each configured to be capable of taking in and discharging air by rotation of an internal fan and ventilate the in-bed space S1.

For example, if the in-bed air conditioner 102 is used in summer, the ventilator 111 functions as an air suction port, and sucks in air in the in-room space S2 and causes the air to flow into the in-bed space S1 via the air passage 112 and circulate along directions of arrows in FIG. 2. The ventilator 113 functions as an air discharge port, and sucks in air in the in-bed space S1 through the air vents of the air passage 114 and discharges air after passage through the air passage 114 to the in-room space S2 along directions of arrows in FIG. 2. In this case, air cooled by the in-room air conditioner 103 flows from a head side to a foot side of the in-bed space S1 to put the in-bed space S1 in a state of keeping head cool and feet warm.

If the in-bed air conditioner 102 is used in winter, the ventilator 113 functions as an air suction port, and sucks in air in the in-room space S2 and causes the air to flow into the in-bed space S1 via the air passage 114 and circulate along directions opposite to the arrows in FIG. 2. The ventilator 111 functions as an air discharge port, and sucks in air in the in-bed space S1 through the air vents of the air passage 112 and discharges air after passage through the air passage 112 to the in-room space S2 along directions opposite to the arrows in FIG. 2. In this case, air warmed by the in-room air conditioner 103 flows from the foot side to the head side of the in-bed space S1 to put the in-bed space S1 in the state of keeping head cool and feet warm.

Note that the configuration of the in-bed air conditioner 102 is not particularly limited to the above-described example and that various changes may be made. One or three or more ventilators may be used or a heating device, such as a heater, may be added. The number, the positions, and the like of air vents of each of the air passages 112 and 114 may be variously changed so as to, for example, prevent air from flowing or being sucked directly into the in-bed space S1.

Referring back to FIG. 1, the air-conditioning controller 105 is communicably connected to the in-bed environment measurer 101, the in-bed air conditioner 102, the in-room air conditioner 103, the in-room environment measurer 104, and the storage 110 using, for example, a wired or wireless network or infrared rays.

The air-conditioning controller 105 determines control details for the in-room air conditioner 103 and the in-bed air conditioner 102 on the basis of the in-bed temperature measured by the in-bed environment measurer 101 and the in-room temperature measured by the in-room environment measurer 104 and gives the determined control details to the in-room air conditioner 103 and the in-bed air conditioner 102.

The storage 110 is composed of a memory, such an external storage device, and stores in advance a target in-bed temperature and target in-room temperatures. The storage 110 outputs the target in-bed temperature and the target in-room temperatures to the air-conditioning controller 105.

Note that various values can be used as the target in-bed temperature and the target in-room temperatures. For example, a user may store preferred values in the storage 110 or a manufacturer or the like of the air-conditioning control system may set favorable values in advance in the storage 110. The configuration of the storage 110 is not particularly limited to the above-described example. For example, various changes, such as providing a memory inside the air-conditioning controller 105 and using the memory as the storage 110, may be made.

The air-conditioning controller 105 is composed of a processor or the like and executes a predetermined program stored in an internal memory or the like. Other embodiments to be described later are the same in the respect.

The air-conditioning controller 105 acquires the in-bed temperature from the in-bed environment measurer 101, acquires the in-room temperature from the in-room environment measurer 104, and controls the operation of the in-bed air conditioner 102 and the wind direction of the in-room air conditioner 103 on the basis of the acquired in-bed temperature and the acquired in-room temperature.

More specifically, the air-conditioning controller 105 acquires the target in-bed temperature and one of the target in-room temperatures from the storage 110, calculates an in-bed temperature difference which is a difference between the in-bed temperature measured by the in-bed environment measurer 101 and the target in-bed temperature for the in-bed space S1, and calculates an in-room temperature difference which is a difference between the in-room temperature measured by the in-room environment measurer 104 and the season-specific target in-room temperature for the in-room space S2.

The air-conditioning controller 105 compares the in-bed temperature difference with the in-room temperature difference and, if the in-bed temperature difference is larger than the in-room temperature difference, brings the in-bed air conditioner 102 into operation to adjust the in-bed temperature. At this time, the air-conditioning controller 105 puts the in-room air conditioner 103 to work and simultaneously changes the wind direction of the in-room air conditioner 103 to a downward direction by turning the outlet 103a downward such that cooled air or heated air from the in-room air conditioner 103 arrives easily at the in-bed air conditioner 102. In this case, the in-bed air conditioner 102 can cool the in-bed space S1 filled with heated air or warm the cooled in-bed space S1 by taking air in the vicinity of the mattress B2 into the in-bed space S1.

If the in-bed temperature difference is not larger than the in-room temperature difference, the air-conditioning controller 105 brings the in-bed air conditioner 102 out of operation, brings the in-room air conditioner 103 into operation and simultaneously changes the wind direction of the in-room air conditioner 103 to an upward direction by turning the outlet 103a upward, and gives priority to in-room temperature adjustment. When the in-bed temperature difference becomes larger than the in-room temperature difference after that, the air-conditioning controller 105 brings the in-bed air conditioner 102 into operation and simultaneously keeps the in-room air conditioner 103 operating with the wind direction changed to the downward direction by turning the outlet 103a downward, as described above, and gives priority to in-bed temperature adjustment.

As described above, when the in-bed air conditioner 102 is operated, the wind direction of the in-room air conditioner 103 is controlled so as to be a bed direction (a direction in which the in-bed air conditioner 102 is located). It is thus possible to efficiently supply air in the temperature-adjusted in-room space S2 to the in-bed air conditioner 102 and implement effective in-bed air conditioning in a shorter time period. At the time of controlling the wind direction of the in-room air conditioner 103 such that the wind direction is the bed direction, the wind direction is desirably controlled so as to face a direction of the air suction port of the in-bed air conditioner 102.

For example, a temperature suitable for sleep for the in-bed space S1 is about 33° C., and a temperature suitable for sleep for the in-room space S2 is 25° C. to 28° C. in summer and is 16° C. to 20° C. in winter (quoted from Shuichiro Shirakawa, "Guide to Good Sleep for Business People").

In the present embodiment, for example, 33° C. is adopted as a target temperature for the in-bed space S1 (the target in-bed temperature). Average values of the above-described temperatures are taken as target temperatures for the in-room space S2 (the target in-room temperatures), 26.5° C. is adopted for summer, and 18° C. is adopted for winter. The air-conditioning controller 105 stores in advance the temperatures.

For example, assuming that it is summer, the in-room air conditioner 103 is at work, the in-room temperature is 27° C., the in-bed air conditioner 102 is not at work, and the in-bed temperature is 35° C., the in-room temperature difference is 0.5° C. and the in-bed temperature difference is 2° C. In this case, since the in-bed temperature difference (2° C.) is larger than the in-room temperature difference (0.5° C.), the air-conditioning controller 105 puts the in-bed air conditioner 102 to work and simultaneously changes the wind direction of the in-room air conditioner 103 to the downward direction by turning the outlet 103a downward such that cooled air from the in-room air conditioner 103 arrives easily at the in-bed air conditioner 102.

Note that the target in-bed temperature and the target in-room temperatures are not particularly limited to the above-described examples and may be variously changed. For example, user preferences may be reflected, and temperatures suitable for respective seasons may be appropriately set.

The air-conditioning controller 105 may bring the in-bed air conditioner 102 into operation to adjust the in-bed temperature only if the in-room temperature measured by the in-room environment measurer 104 is closer to the target in-bed temperature than the in-bed temperature measured by the in-bed environment measurer 101. In this case, the in-bed air conditioner 102 can bring the temperature of the in-bed space S1 close to the target in-bed temperature in a shorter time period by taking air in the vicinity of the mattress B2 which is close to the target in-bed temperature into the in-bed space S1.

As described above, in the present embodiment, the in-bed temperature and the in-room temperature are measured, and the in-bed temperature difference that is a difference between the measured in-bed temperature and the target in-bed temperature and the in-room temperature difference that is a difference between the measured in-room temperature and the target in-room temperature are calculated. Since the in-bed air conditioner 102 is brought into operation to adjust the in-bed temperature if the in-bed temperature difference is larger than the in-room temperature difference, the in-bed temperature can be adjusted by giving priority to the in-bed space S1 with the larger temperature difference. It is thus possible to implement effective in-bed air conditioning in a shorter time period and curb power consumption.

Note that although the air-conditioning controller 105 is provided separately from the in-bed air conditioner 102 and the in-room air conditioner 103 in the present embodiment, the air-conditioning controller 105 is not particularly limited to the example. Various changes, such as incorporating the air-conditioning controller 105 in the in-bed air conditioner 102 or the in-room air conditioner 103, may be made.

In the present embodiment, the in-room air conditioner 103 is operated with the wind direction set to the downward direction when the in-bed air conditioner 102 is in operation. The present disclosure, however, is not particularly limited to the example. Various changes, such as bringing the in-room air conditioner 103 out of operation if the in-room temperature difference is smaller or in other cases, may be made.

Control methods for the air-conditioning controller 105 can be arbitrarily combined. For example, if the in-room temperature is closer to the target in-bed temperature than the in-bed temperature and the in-bed temperature difference is larger than the in-room temperature difference, the in-bed air conditioner 102 may be brought into operation to adjust the in-bed temperature. Other embodiments (to be described later) are the same in the respects.

Second Embodiment

The above-described first embodiment has described an example in which the air-conditioning controller 105 is installed in a room where the user HB sleeps. A cloud server or the like which is connected via a network, such as the Internet, may execute functions of the air-conditioning controller 105 for the air-conditioning controller 105. The present embodiment will describe an air-conditioning control system using a server which is connected via a network.

Figure 3:
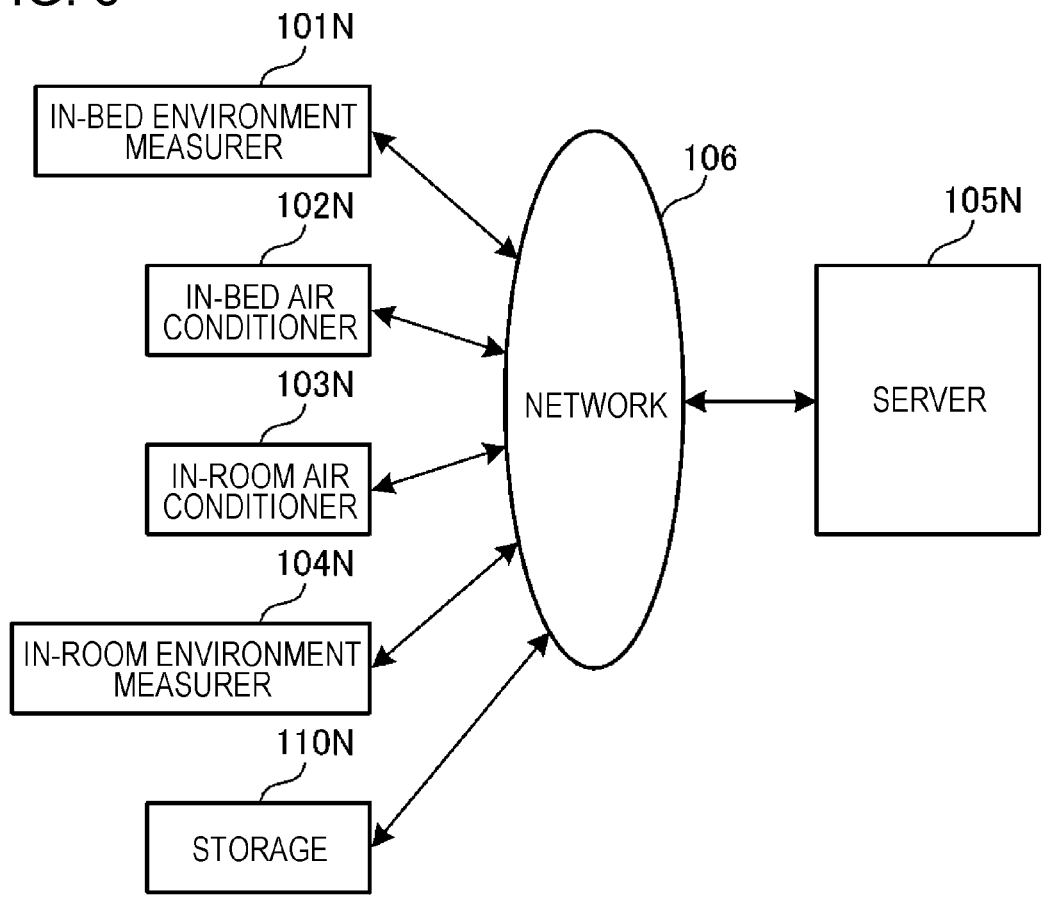
FIG. 3 is a diagram showing an example of the configuration of an air-conditioning control system according to a second embodiment of the present disclosure.

FIG. 3 is a diagram showing an example of the configuration of an air-conditioning control system according to a second embodiment of the present disclosure. The air-conditioning control system shown in FIG. 3 includes an in-bed environment measurer 101N, an in-bed air conditioner 102N, an in-room air conditioner 103N, an in-room environment measurer 104N, a storage 110N, and a server 105N. Note that although FIG. 3 shows an example in which one in-bed environment measurer 101N and the like are connected to the server 105N via a network 106, the present disclosure is not particularly limited to the example. A plurality of in-bed environment measurers 101N and the like may be network-connected, and the server 105N may control the devices.

The in-bed environment measurer 101N, the in-bed air conditioner 102N, the in-room air conditioner 103N, the in-room environment measurer 104N, the storage 110N, and the server 105N are configured in the same manner as the in-bed environment measurer 101, the in-bed air conditioner 102, the in-room air conditioner 103, the in-room environment measurer 104, the storage 110, and the air-conditioning controller 105 shown in FIG. 1. Each of the in-bed environment measurer 101N, the in-bed air conditioner 102N, the in-room air conditioner 103N, the in-room environment measurer 104N, the storage 110N, and the server 105N includes a communicator (not shown) for network connection inside.

The in-bed environment measurer 101N, the in-bed air conditioner 102N, the in-room air conditioner 103N, the in-room environment measurer 104N, and the storage 110N are communicably connected to the server 105N via the network 106 using the internal communicators. Note that the configurations of the communicators are not particularly limited to the above-described example and that various changes, such as connecting the in-bed environment measurer 101N, the in-bed air conditioner 102N, the in-room air conditioner 103N, the in-room environment measurer 104N, and the storage 110N to the network 106 via a communication device such as a broadband router, may be made.

Figure 4:
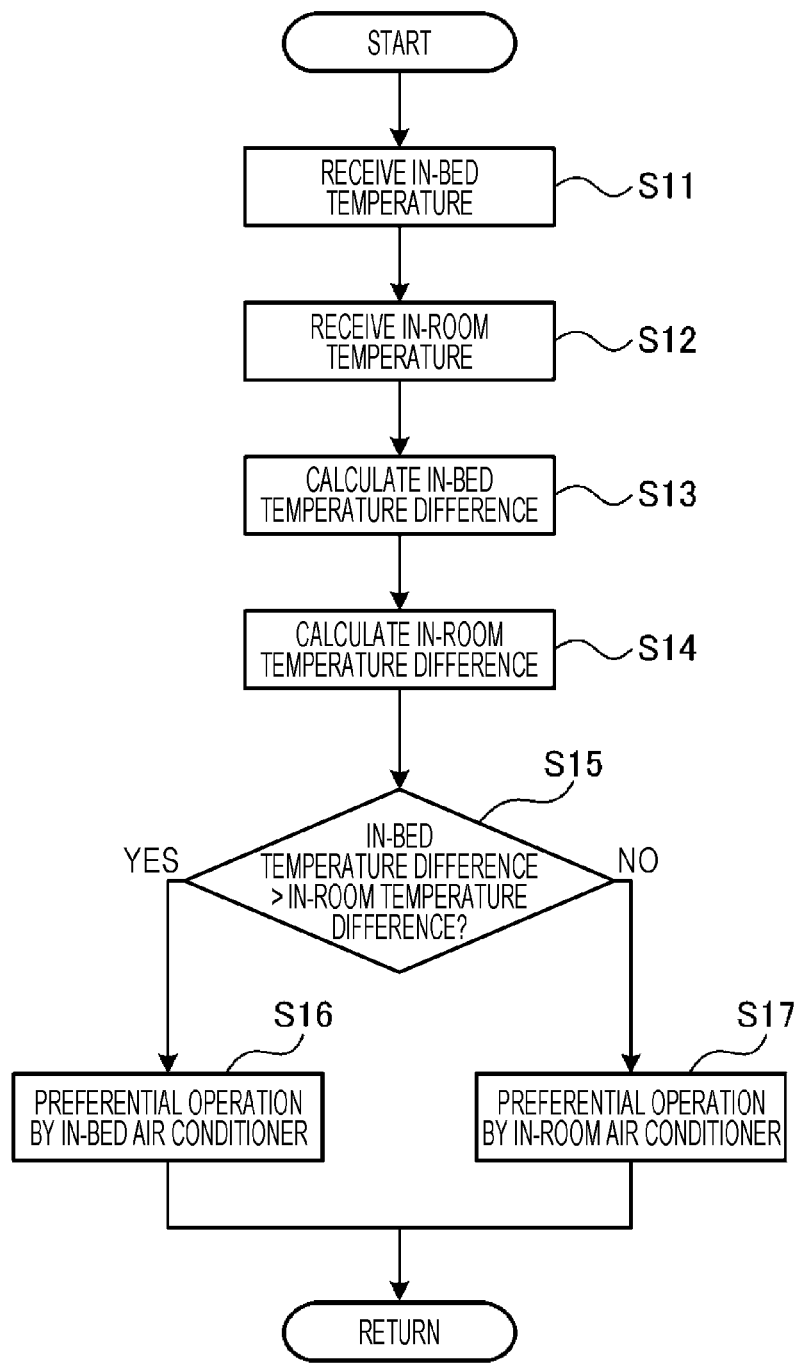
FIG. 4 is a flowchart showing an example of an in-bed air conditioning process by a server shown in FIG. 3.

FIG. 4 is a flowchart showing an example of an in-bed air conditioning process by the server 105N shown in FIG. 3.

First, the server 105N requests measurement of an in-bed temperature from the in-bed environment measurer 101N via the network 106, receives the in-bed temperature transmitted from the in-bed environment measurer 101N, and receives a target in-bed temperature from the storage 110N (step S11).

The server 105N then requests measurement of an in-room temperature from the in-room environment measurer 104N via the network 106, receives the in-room temperature transmitted from the in-room environment measurer 104N, and receives a target in-room temperature from the storage 110N (step S12).

The server 105N then calculates an in-bed temperature difference which is a difference between the in-bed temperature measured by the in-bed environment measurer 101N and the target in-bed temperature for an in-bed space S1 (step S13).

The server 105N then calculates an in-room temperature difference which is a difference between the in-room temperature measured by the in-room environment measurer 104N and the season-specific target in-room temperature for an in-room space S2 (step S14).

The server 105N then compares the in-bed temperature difference with the in-room temperature difference and judges whether the in-bed temperature difference is larger than the in-room temperature difference (step S15).

If the in-bed temperature difference is larger than the in-room temperature difference (YES in step S15), the server 105N brings the in-bed air conditioner 102N into operation to adjust the in-bed temperature, puts the in-room air conditioner 103N to work, transmits a control command to change a wind direction of the in-room air conditioner 103N to a downward direction to the in-bed air conditioner 102N and the in-room air conditioner 103N, and causes the in-bed air conditioner 102N to execute preferential operation (step S16). After that, the flow returns to step S11 to repeat the subsequent processes.

On the other hand, if the in-bed temperature difference is not larger than the in-room temperature difference (NO in step S15), the server 105N brings the in-bed air conditioner 102N out of operation, brings the in-room air conditioner 103N into operation, transmits a control command to change the wind direction of the in-room air conditioner 103N to an upward direction to the in-bed air conditioner 102N and the in-room air conditioner 103N, and causes the in-room air conditioner 103N to execute preferential operation (step S17). After that, the flow returns to step S11 to repeat the subsequent processes.

With the above-described process, in the present embodiment, the in-bed temperature difference which is a difference between the in-bed temperature and the target in-bed temperature and the in-room temperature difference which is a difference between the in-room temperature and the predetermined target in-room temperature are calculated. Since the in-bed air conditioner 102N is brought into operation to adjust the in-bed temperature if the in-bed temperature difference is larger than the in-room temperature difference, the in-bed temperature can be adjusted by giving priority to the in-bed space S1 with the larger temperature difference. It is thus possible to implement effective in-bed air conditioning in a shorter time period.

Note that although the present embodiment has described an example in which the server 105N is used instead of the air-conditioning controller 105 according to the first embodiment, the present disclosure is not particularly limited to the example. A server may be used instead of other air-conditioning controllers (to be described later), and same effects can be obtained.

Third Embodiment

In the above-described first embodiment, the in-bed air conditioner 102 and the in-room air conditioner 103 are controlled on the basis of an in-bed temperature and an in-room temperature. The present embodiment will describe an air-conditioning control system which controls an in-bed air conditioner and an in-room air conditioner on the basis of an in-bed humidity and an in-room humidity in addition to an in-bed temperature and an in-room temperature.

Figure 5:
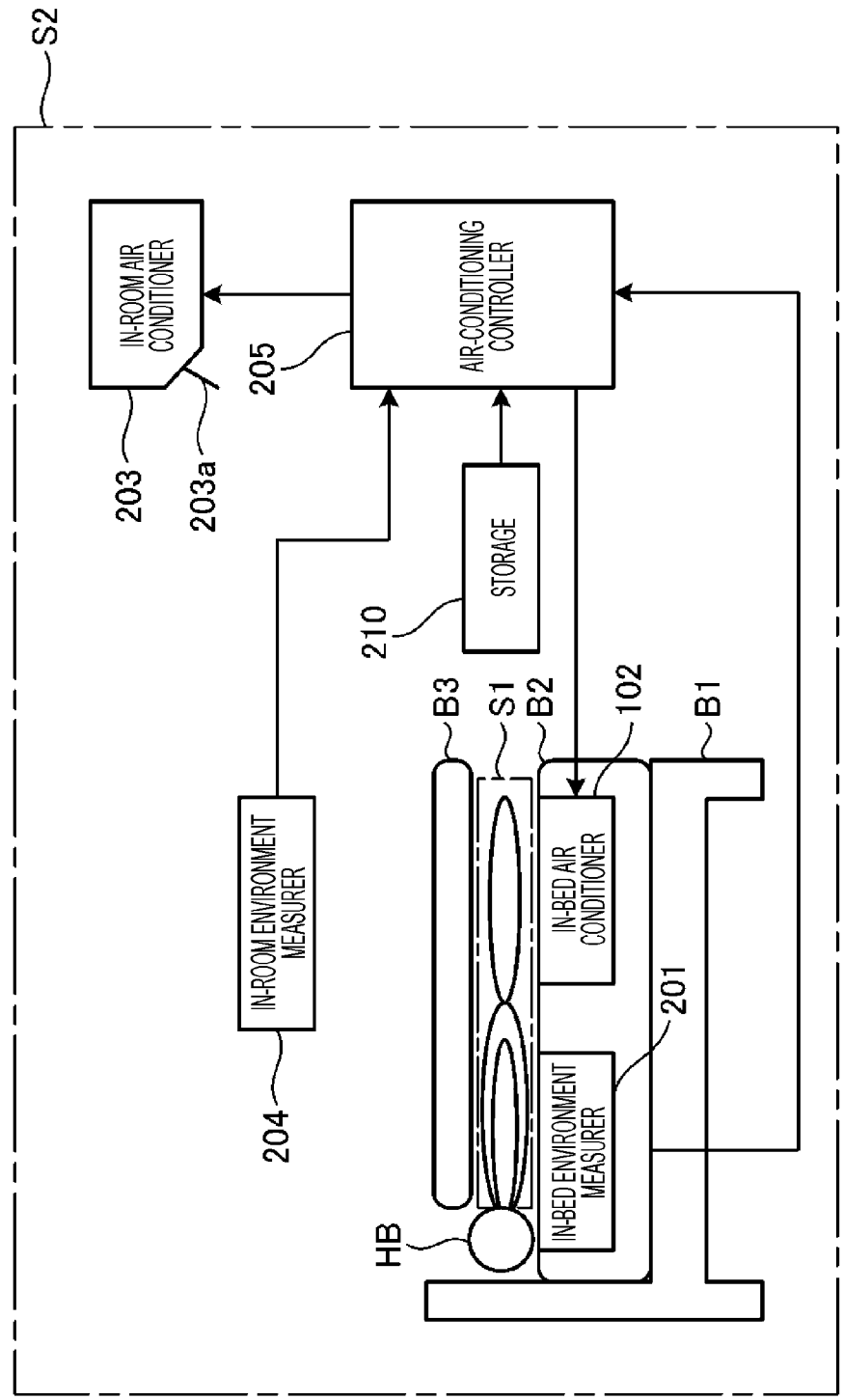
FIG. 5 is a diagram showing an example of the configuration of an air-conditioning control system according to a third embodiment of the present disclosure.

FIG. 5 is a diagram showing an example of the configuration of an air-conditioning control system according to a third embodiment of the present disclosure. The air-conditioning control system shown in FIG. 5 includes an in-bed environment measurer 201, an in-bed air conditioner 102, an in-room air conditioner 203, an in-room environment measurer 204, an air-conditioning controller 205, and a storage 210. Note that same components as those in FIG. 1 are denoted by same reference characters in FIG. 5 and that a detailed description thereof will be omitted.

The in-bed environment measurer 201 is composed of a temperature sensor, a humidity sensor, and the like and is attached to a predetermined position in a mattress B2, for example, the vicinity of an upper body of a user HB. The in-bed environment measurer 201 measures a temperature (an in-bed temperature) and a humidity (an in-bed humidity) of an in-bed space S1 and outputs the temperature and humidity of the in-bed space S1 to the air-conditioning controller 205.

The in-room environment measurer 204 is composed of a temperature sensor, a humidity sensor, and the like and is attached to a predetermined position in an in-room space S2, for example, a middle position in the in-room space S2. The in-room environment measurer 204 measures a temperature (an in-room temperature) and a humidity (an in-room humidity) of the in-room space S2 and outputs the temperature and humidity of the in-room space S2 to the air-conditioning controller 205.

Note that the configuration of the in-bed environment measurer 201 is not particularly limited to the above-described example and that the in-bed environment measurer 201 may be, for example, installed in a comforter B3 or at a bed B1 instead of being installed in the mattress B2. The number of in-bed environment measurers 201 is not limited to one, and a plurality of in-bed environment measurers 201 may be installed. The configuration of the in-room environment measurer 204 is not particularly limited to the above-described example, and the in-room environment measurer 204 may be provided, for example, inside the in-room air conditioner 203 or in the vicinity of a head of the bed B1.

The in-room air conditioner 203 is composed of, for example, an air conditioner and is attached to an upper portion of one of walls forming the in-room space S2. The in-room air conditioner 203 can perform cooling operation, heating operation, and dehumidification operation and adjusts the temperature and humidity of the in-room space S2 in accordance with an operating state, a setup temperature, and the like. The in-room air conditioner 203 includes an outlet (louver) 203a and can change a wind direction.

The in-bed air conditioner 102 is configured in the same manner as the in-bed air conditioner 102 shown in FIGS. 1 and 2.

The air-conditioning controller 205 is communicably connected to the in-bed environment measurer 201, the in-bed air conditioner 102, the in-room air conditioner 203, the in-room environment measurer 204, and the storage 210 using, for example, a wired or wireless network or infrared rays. The air-conditioning controller 205 determines control details for the in-room air conditioner 203 and the in-bed air conditioner 102 on the basis of the in-bed temperature and the in-bed humidity measured by the in-bed environment measurer 201 and the in-room temperature and the in-room humidity measured by the in-room environment measurer 204 and gives the determined control details to the in-room air conditioner 203 and the in-bed air conditioner 102.

The storage 210 is composed of a memory, such as an external storage device, and stores in advance a target in-bed comfort level and target in-room comfort levels. The storage 210 outputs the target in-bed comfort level and the target in-room comfort levels to the air-conditioning controller 205.

Note that various values can be used as the target in-bed comfort level and the target in-room comfort levels. For example, a user may store preferred values in the storage 210 or a manufacturer or the like of the air-conditioning control system may set favorable values in advance in the storage 210. The configuration of the storage 210 is not particularly limited to the above-described example. For example, various changes, such as providing a memory inside the air-conditioning controller 205 and using the memory as the storage 210, may be made.

The air-conditioning controller 205 acquires the in-bed temperature and the in-bed humidity from the in-bed environment measurer 201, acquires the in-room temperature and the in-room humidity from the in-room environment measurer 204, and acquires the target in-bed comfort level and one of the target in-room comfort levels from the storage 210. The air-conditioning controller 205 calculates an in-bed comfort level which serves as a barometer for in-bed comfort using the in-bed temperature and the in-bed humidity and calculates an in-bed comfort level difference which is a difference between the in-bed comfort level and the target in-bed comfort level. The air-conditioning controller 205 calculates an in-room comfort level which serves as a barometer for in-room comfort using the in-room temperature and the in-room humidity and calculates an in-room comfort level difference which is a difference between the in-room comfort level and the target in-room comfort level. The air-conditioning controller 205 controls the operation of the in-bed air conditioner 102 and the wind direction of the in-room air conditioner 203 on the basis of the in-bed comfort level difference and the in-room comfort level difference.

More specifically, the air-conditioning controller 205 calculates the in-bed comfort level serving as a barometer for comfort of the in-bed space S1, using the in-bed temperature and the in-bed humidity measured by the in-bed environment measurer 201, and calculates the in-bed comfort level difference of the in-bed space S1 that is a difference between the calculated in-bed comfort level and the target in-bed comfort level for the in-bed space S1. The air-conditioning controller 205 also calculates the in-room comfort level serving as a barometer for comfort of the in-room space S2, using the in-room temperature and the in-room humidity measured by the in-room environment measurer 204, and calculates the in-room comfort level difference that is a difference between the calculated in-room comfort level and the season-specific target in-room comfort level for the in-room space S2.

The air-conditioning controller 205 compares the in-bed comfort level difference with the in-room comfort level difference and, if the in-bed comfort level difference is larger than the in-room comfort level difference, brings the in-bed air conditioner 102 into operation to adjust the in-bed temperature. At this time, the air-conditioning controller 205 puts the in-room air conditioner 203 to work and simultaneously changes the wind direction of the in-room air conditioner 203 to a downward direction by turning the outlet 203a downward such that cooled air or heated air from the in-room air conditioner 203 arrives easily at the in-bed air conditioner 102. In this case, the in-bed air conditioner 102 can cool the in-bed space S1 filled with heated air or warm the cooled in-bed space S1 by taking air in the vicinity of the mattress B2 into the in-bed space S1.

If the in-bed comfort level difference is not larger than the in-room comfort level difference, the air-conditioning controller 205 brings the in-bed air conditioner 102 out of operation, brings the in-room air conditioner 203 into operation and simultaneously changes the wind direction of the in-room air conditioner 203 to an upward direction by turning the outlet 203a upward, and gives priority to in-room temperature adjustment. When the in-bed comfort level difference becomes larger than the in-room comfort level difference after that, the air-conditioning controller 205 brings the in-bed air conditioner 102 into operation and simultaneously keeps the in-room air conditioner 203 operating with the wind direction changed to the downward direction by turning the outlet 203a downward, as described above, and gives priority to in-bed temperature and in-bed humidity adjustment.

As described above, when the in-bed air conditioner 102 is operated, the wind direction of the in-room air conditioner 203 is controlled so as to be a bed direction (a direction in which the in-bed air conditioner 102 is located). It is thus possible to efficiently supply air in a temperature- and humidity-adjusted room interior to the in-bed air conditioner 102 and implement effective in-bed air conditioning in a shorter time period. At the time of controlling the wind direction of the in-room air conditioner 203 such that the wind direction is the bed direction, the wind direction is desirably controlled so as to face a direction of an air suction port of the in-bed air conditioner 102.

For example, a temperature suitable for sleep for the in-bed space S1 is about 33° C., and a humidity is about 50%. A temperature suitable for sleep for the in-room space S2 is 25° C. to 28° C. in summer and is 16° C. to 20° C. in winter, and a humidity is not more than 70% in summer and not less than 50% in winter.

In the present embodiment, for example, the discomfort index that represents greater comfort when having a lower value is adopted for each of the in-bed comfort level and the in-room comfort level. If the discomfort index is adopted, a target comfort level (the target in-bed comfort level) for the in-bed space S1 is 82. Assuming that a target temperature for the in-room space S2 in summer is 26.5° C. and a target humidity is 70%, a target comfort level (the target in-room comfort level) for the in-room space S2 is 75.5. The air-conditioning controller 205 stores in advance such temperatures, humidities, and discomfort indexes and calculates the discomfort index for the in-bed space S1 and the discomfort index for the in-room space S2 using (discomfort index)=$0.81Td+0.01H(0.99Td-14.3)+46.3$ (where Td=temperature, and H=humidity).

For example, assume that it is summer, the in-room air conditioner 203 is at work, the in-room temperature is 28° C., the in-room humidity is 80%, the in-bed air conditioner 102 is not at work, the in-bed temperature is 35° C., and the in-bed humidity is 80%. Since the discomfort index for the in-room space S2 is 79 and the discomfort index for the in-bed space S1 is 90, the in-room comfort level difference is 3.5 and the in-bed comfort level difference is 8. In this case, since the in-bed comfort level difference (8) is larger than the in-room comfort level difference (3.5), the air-conditioning controller 205 puts the in-bed air conditioner 102 to work and simultaneously changes the wind direction of the in-room air conditioner 203 to the downward direction by turning the outlet 203a downward such that cooled air from the in-room air conditioner 203 arrives easily at the in-bed air conditioner 102.

Note that the in-bed comfort level and the in-room comfort level are not particularly limited to the above-described example using the discomfort index. For example, any other index serving as a barometer for in-bed comfort may be used or user preferences may be reflected, and indexes suitable for respective seasons may be appropriately set.

The air-conditioning controller 205 may bring the in-bed air conditioner 102 into operation to adjust the in-bed temperature only if the in-room comfort level (for example, an in-room discomfort index) calculated from the in-room temperature and the in-room humidity measured by the in-room environment measurer 204 is closer to the target in-bed comfort level (for example, a target in-bed discomfort index) than the in-bed comfort level (for example, an in-bed discomfort index) calculated from the in-bed temperature and the in-bed humidity measured by the in-bed environment measurer 201. In this case, the in-bed air conditioner 102 can bring the in-bed comfort level of the in-bed space S1 close to the target in-bed comfort level in a shorter time period by taking air in the vicinity of the mattress B2 which is close to the target in-bed comfort level into the in-bed space S1.

For example, if the in-room temperature is 28° C., the in-room humidity is 40%, the in-bed temperature is 35° C., and the in-bed humidity is 70%, the in-bed air conditioner 102 may be brought into operation. Meanwhile, if the in-room temperature is 18° C., the in-room humidity is 40%, the in-bed temperature is 25° C., and the in-bed humidity is 40%, the in-bed air conditioner 102 may be brought out of operation. Note that although whether to bring the in-bed air conditioner 102 into or out of operation is determined using the discomfort index as a barometer in the above-described example, the present disclosure is not particularly limited to the example. For example, whether to bring the in-bed air conditioner 102 into or out of operation may be determined using a temperature and/or a humidity as a barometer.

As described above, in the present embodiment, the in-bed humidity and the in-room humidity are measured in addition to the in-bed temperature and the in-room temperature, the in-bed comfort level serving as a barometer for in-bed comfort is calculated using the measured in-bed temperature and in-bed humidity, the in-bed comfort level difference that is a difference between the in-bed comfort level and the target in-bed comfort level is calculated, the in-room comfort level serving as a barometer for in-room comfort is calculated using the measured in-room temperature and in-room humidity, and the in-room comfort level difference that is a difference between the in-room comfort level and the target in-room comfort level is calculated. Since the in-bed air conditioner 102 is brought into operation to adjust the in-bed temperature if the in-bed comfort level difference is larger than the in-room comfort level difference, the in-bed temperature can be adjusted by giving priority to the in-bed space S1 with a larger difference from a target comfort level. It is thus possible to make a bed interior more comfortable in a shorter time period and curb power consumption.

Fourth Embodiment

In the above-described first embodiment, the in-bed air conditioner 102 and the in-room air conditioner 103 are controlled on the basis of an in-bed temperature and an in-room temperature. The present embodiment will describe an air-conditioning control system which measures biological information of a person, judges a sleep state of the person on the basis of a result of measuring the biological information, and controls an in-bed air conditioner and an in-room air conditioner on the basis of the sleep state in addition to an in-bed temperature and an in-room temperature.

Figure 6:
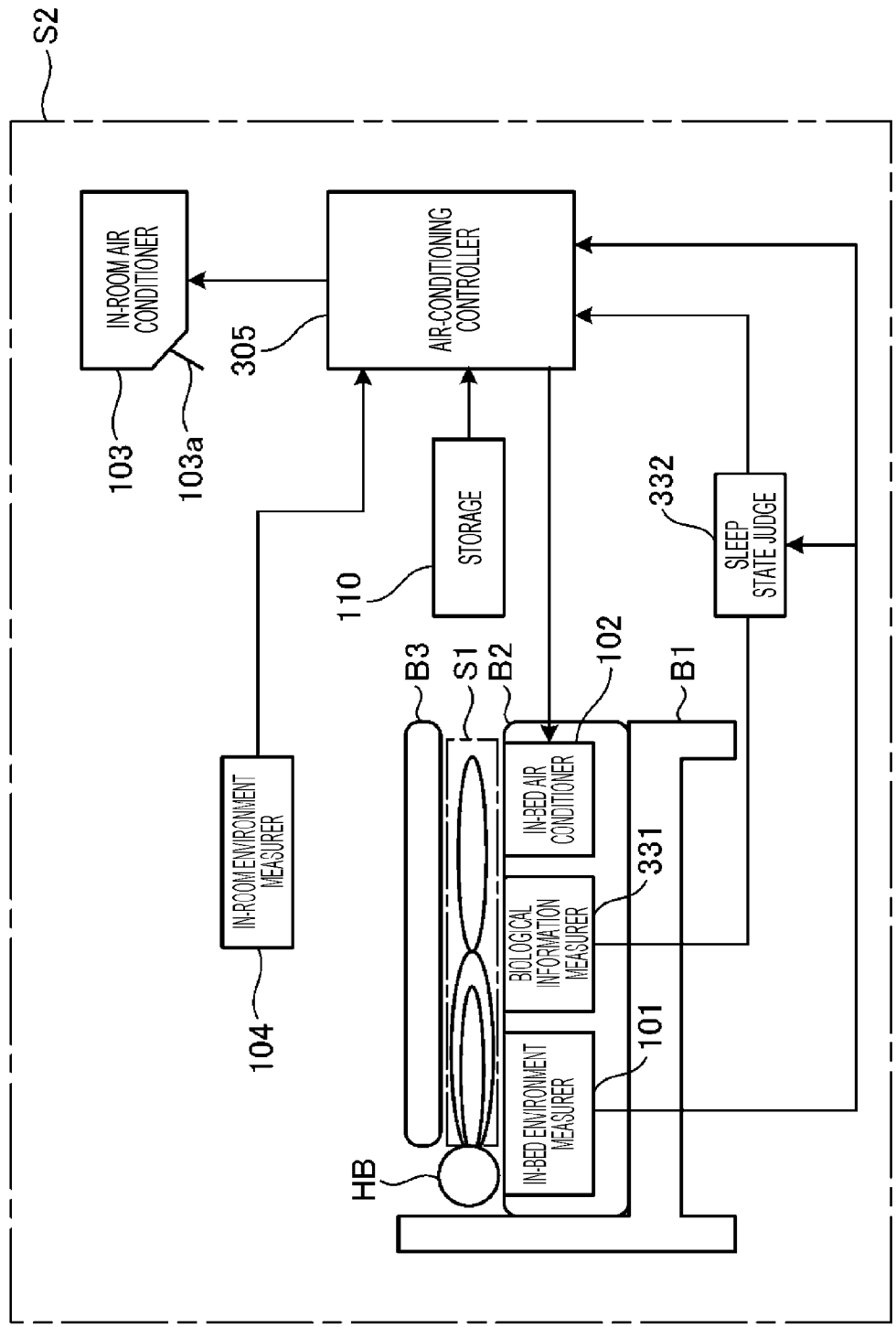
FIG. 6 is a diagram showing an example of the configuration of an air-conditioning control system according to a fourth embodiment of the present disclosure.

FIG. 6 is a diagram showing an example of the configuration of an air-conditioning control system according to a fourth embodiment of the present disclosure. The air-conditioning control system shown in FIG. 6 includes an in-bed environment measurer 101, an in-bed air conditioner 102, an in-room air conditioner 103, an in-room environment measurer 104, a storage 110, a biological information measurer 331, a sleep state judge 332, and an air-conditioning controller 305. Note that same components as those in FIG. 1 are denoted by same reference characters in FIG. 6 and that a detailed description thereof will be omitted.

The biological information measurer 331 measures biological information. Examples of the biological information include body motion data. For example, the biological information measurer 331 is composed of a body motion sensor having an acceleration sensor, a gyroscope sensor, or the like and is attached to a predetermined position in a mattress B2, such as the vicinity of the waist of a user HB. The biological information measurer 331 measures body motion data (for example, the frequency of tossing and turning) representing motion of the user HB during sleep as biological information and outputs the biological information to the sleep state judge 332.

Note that the configuration of the biological information measurer 331 and biological information are not particularly limited to the above-described examples. For example, biological information may be a heart rate, and the biological information measurer 331 may be a heart rate sensor composed of, for example, a radio-frequency sensor which measures heartbeat (a heart-rate signal) of the user HB in a non-contact manner. Alternatively, for example, biological information may be a respiration rate, and the biological information measurer 331 may be a respiration sensor composed of, for example, a radio-frequency sensor which measures respiration (a respiration signal) of the user HB in a non-contact manner. Alternatively, the biological information measurer 331 may use a plurality of sensors in combination.

The sleep state judge 332 judges a state of a person on the basis of biological information measured by the biological information measurer 331 and outputs a result of the judgment to the air-conditioning controller 305. More specifically, the sleep state judge 332 judges, on the basis of the biological information, whether the person is in a sleeping state. Various methods, such as comparing the biological information with a threshold, comparing a feature quantity of the biological information with a predetermined feature quantity, and inputting the biological information to a machine learning model which performs state judgment and obtaining output, can be adopted as a judgment method. For example, if the amount of body motion (the frequency of tossing and turning) indicated by body motion data is larger than a threshold, it can be judged that the person is in a light sleep. Note that a known judgment method (see, for example, Japanese Unexamined Patent Application Publication No. 2017-000211), such as judging a waking period, a sleep period, or the like in accordance with the amount of body motion, can be used as a sleep state judgment method according to the present embodiment.

The sleep state judge 332 judges the degree of difficulty in sleeping well for the user HB during sleep from body motion data measured by the biological information measurer 331 and an in-bed temperature measured by the in-bed environment measurer 101. If it is hot in an in-bed space S1 in summer, the frequency of tossing and turning increases. However, the frequent tossing and turning does not always mean difficulty in sleeping well. For this reason, in the present embodiment, the degree of difficulty in sleeping well for the user HB is judged with reference to a rise in temperature of the in-bed space S1 and the frequency of tossing and turning indicated by body motion data. The degree of difficulty in sleeping well for the user HB can be accurately judged. For example, a known method (Japanese Patent No. 5237845) can be used as a method for judging the degree of difficulty in sleeping well. Note that the configuration of the sleep state judge 332 is not particularly limited to the above-described example and that various changes, such as incorporating the sleep state judge 332 in the air-conditioning controller 305 or the like, may be made.

The air-conditioning controller 305 is communicably connected to the in-bed environment measurer 101, the in-bed air conditioner 102, the in-room air conditioner 103, the in-room environment measurer 104, and the sleep state judge 332 using, for example, a wired or wireless network or infrared rays. The air-conditioning controller 305 controls the in-bed air conditioner 102 and the in-room air conditioner 103 on the basis of the in-bed temperature measured by the in-bed environment measurer 101, an in-room temperature measured by the in-room environment measurer 104, and a sleep state judged by the sleep state judge 332.

More specifically, if the sleep state judged by the sleep state judge 332 indicates being in bed (for example, a state in which the user HB is between the mattress B2 and a comforter B3), the air-conditioning controller 305 brings the in-bed air conditioner 102 into operation to adjust the in-bed temperature. At this time, the air-conditioning controller 305 puts the in-room air conditioner 103 to work and simultaneously changes a wind direction of the in-room air conditioner 103 to a downward direction by turning an outlet 103a downward such that cooled air or heated air from the in-room air conditioner 103 arrives easily at the in-bed air conditioner 102. In this case, the in-bed air conditioner 102 can cool the in-bed space S1 filled with heated air or warm the cooled in-bed space S1 by taking air in the vicinity of the mattress B2 into the in-bed space S1.

If the sleep state judged by the sleep state judge 332 indicates having got out of bed, the air-conditioning controller 305 brings the in-bed air conditioner 102 into operation to dry the in-bed space S1. At this time, the air-conditioning controller 305 puts the in-room air conditioner 103 to work to perform dehumidification operation or the like and simultaneously changes the wind direction of the in-room air conditioner 103 to the downward direction by turning the outlet 103a downward such that dry air from the in-room air conditioner 103 arrives easily at the in-bed air conditioner 102. In this case, the in-bed air conditioner 102 takes dry air in the vicinity of the mattress B2 into the in-bed space S1, thereby allowing drying of the humid in-bed space S1 and drying of the mattress B2 and the comforter B3 with absorbed moisture.

If the sleep state judged by the sleep state judge 332 indicates having fallen asleep, when the in-room air conditioner 103 is in cooling or dehumidification operation, the air-conditioning controller 305 brings the in-bed air conditioner 102 into operation and simultaneously changes the wind direction of the in-room air conditioner 103 to the downward direction by turning the outlet 103a downward, and slightly (for example, by 1° C.) raises a setup temperature of the in-room air conditioner 103. On the other hand, when the in-room air conditioner 103 is in heating operation, the air-conditioning controller 305 brings the in-bed air conditioner 102 out of operation and lowers the setup temperature of the in-room air conditioner 103 by 6° C. to 7° C. by, for example, changing the setup temperature from 22° C. to 16° C.

In this case, temperature-adjusted air in the vicinity of the mattress B2 is taken into the in-bed space S1 in summer. This makes it possible to maintain a state comfortable for sleep in the in-bed space S1 while raising the temperature such that an in-room space S2 is not cooled too much. It is possible in winter to inhibit the in-room space S2 from being excessively heated while maintaining the state comfortable for sleep in the in-bed space S1. Note that although the in-bed air conditioner 102 is brought out of operation when the in-room air conditioner 103 is in heating operation, the present disclosure is not particularly limited to the example. If a temperature of the in-bed space S1 changes, the in-bed air conditioner 102 may be brought into operation.

If the sleep state judged by the sleep state judge 332 indicates having a light sleep before rising, when the in-room air conditioner 103 is in cooling or dehumidification operation, the air-conditioning controller 305 brings the in-bed air conditioner 102 into operation and simultaneously changes the wind direction of the in-room air conditioner 103 to the downward direction by turning the outlet 103a downward, and slightly (for example, by 0.5° C. to 1° C.) raises the setup temperature of the in-room air conditioner 103. On the other hand, when the in-room air conditioner 103 is in heating operation, the air-conditioning controller 305 brings the in-bed air conditioner 102 into operation and simultaneously raises the setup temperature of the in-room air conditioner 103, for example, from 16° C. described above by 6° C. to 7° C.

In this case, a deep body temperature of the user HB having a light sleep before rising rises due to a biological mechanism. It is possible to promote a rise in the deep body temperature of the user HB by raising a temperature of the in-room space S2 and adjust the temperature of the in-room space S2 to an environmental temperature at which the user HB after rising can easily perform activity. Note that although the in-bed air conditioner 102 is brought into operation when the in-room air conditioner 103 is in heating operation, the present disclosure is not particularly limited to the example. The in-bed air conditioner 102 may be brought out of operation, as needed.

If the sleep state judge 332 judges from body motion data and the in-bed temperature that the user HB during sleep has difficulty in sleeping well, the air-conditioning controller 305 brings the in-bed air conditioner 102 into operation and simultaneously lowers the setup temperature of the in-room air conditioner 103. For example, the air-conditioning controller 305 changes the wind direction of the in-room air conditioner 103 to the downward direction by turning the outlet 103a downward, causes the in-room air conditioner 103 to perform cooling or dehumidification operation with the setup temperature lowered by, for example, 1° C. to 2° C., and brings the in-bed air conditioner 102 into operation. In this case, the temperature of the in-room space S2 can be lowered to a temperature suitable for sleep, and the temperature of the in-bed space S1 can be lowered using air in the in-room space S2 with the lowered temperature. This puts the in-bed space S1 in a state comfortable for sleep.

As described above, in the present embodiment, biological information of the user HB is measured, a sleep state of the user HB is judged on the basis of a result of measuring the biological information, and the in-bed air conditioner 102 and the in-room air conditioner 103 are controlled on the basis of the measured in-bed temperature and in-room temperature and the judged sleep state. It is thus possible to air-condition the in-bed space S1 using air in the in-room space S2 temperature-adjusted in accordance with the sleep state of the user HB and implement in-bed air conditioning suitable for the sleep state of the user HB.

Fifth Embodiment

In the above-described first embodiment, the in-bed air conditioner 102 and the in-room air conditioner 103 are controlled on the basis of an in-bed temperature and an in-room temperature. The present embodiment will describe an air-conditioning control system which controls an in-bed air conditioner and an in-room air conditioner on the basis of an action schedule of a user in addition to an in-bed temperature and an in-room temperature.

Figure 7:
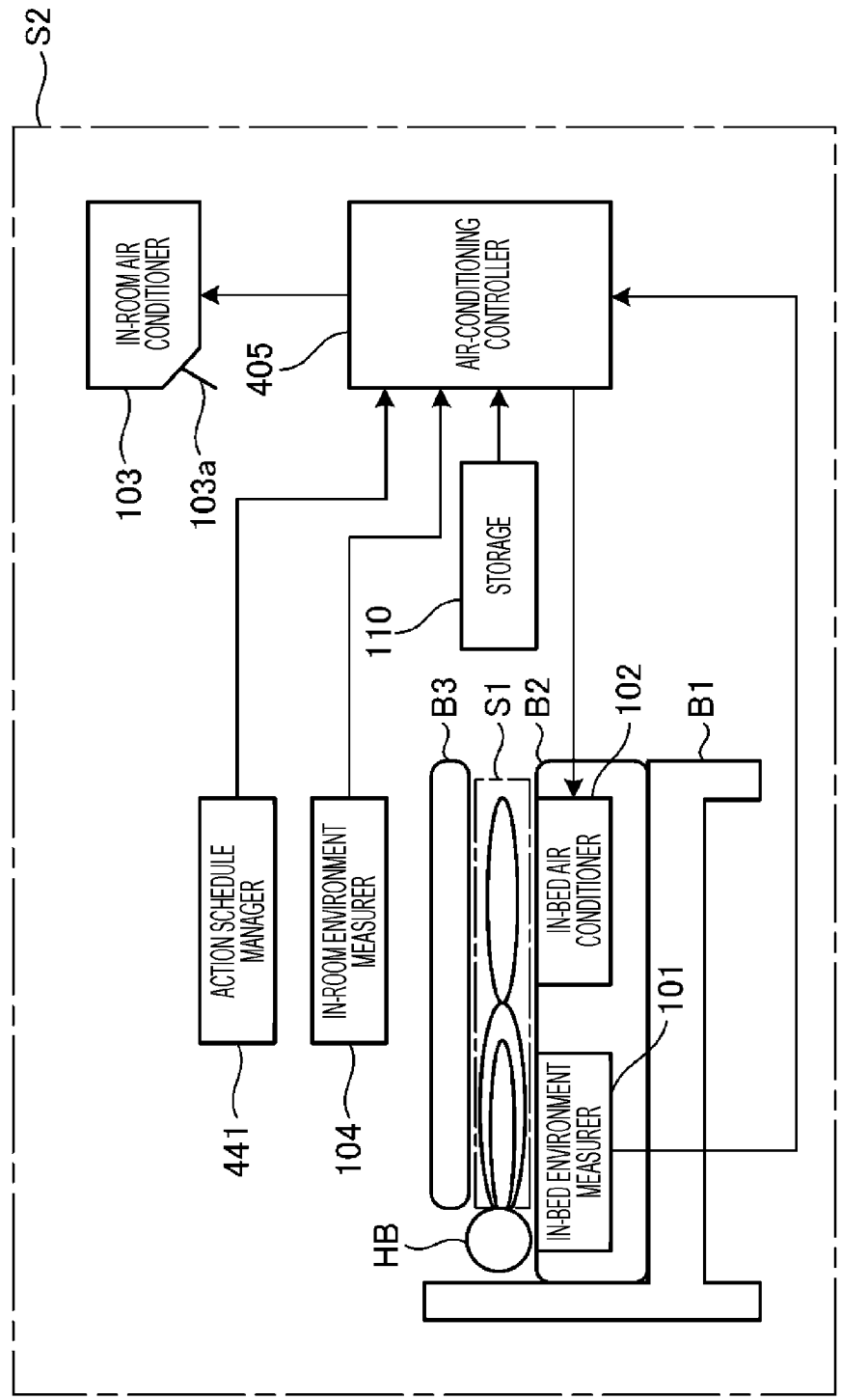
FIG. 7 is a diagram showing an example of the configuration of an air-conditioning control system according to a fifth embodiment of the present disclosure.

FIG. 7 is a diagram showing an example of the configuration of an air-conditioning control system according to a fifth embodiment of the present disclosure. The air-conditioning control system shown in FIG. 7 includes an in-bed environment measurer 101, an in-bed air conditioner 102, an in-room air conditioner 103, an in-room environment measurer 104, a storage 110, an action schedule manager 441, and an air-conditioning controller 405. Note that same components as those in FIG. 1 are denoted by same reference characters in FIG. 7 and that a detailed description thereof will be omitted.

The action schedule manager 441 manages an action schedule of a user HB. For example, the action schedule manager 441 receives an input of time of return of the user HB and determines an estimated bedtime from the time of return. For inputting a time of return or the like of the user HB to the action schedule manager 441, various input methods, such as inputting to the action schedule manager 441 by the user HB or automatic inputting using location information of an information terminal such as a smartphone carried by the user HB, may be used. Note that a method for managing an action schedule including a time of return and the like is not particularly limited to the above-described example and that various changes, such as storing a time of return, a bedtime, and the like in a predetermined server and acquiring the times from the server, may be made.

The air-conditioning controller 405 refers to the action schedule manager 441 and acquires an estimated bedtime of the user HB. The air-conditioning controller 405 brings the in-bed air conditioner 102 into operation a predetermined time period (for example, 30 minutes) before the estimated bedtime to adjust a temperature of an in-bed space S1. At this time, the air-conditioning controller 405 puts the in-room air conditioner 103 to work and simultaneously changes a wind direction of the in-room air conditioner 103 to a downward direction by turning an outlet 103a downward. The air-conditioning controller 405 can efficiently supply air in a temperature-adjusted in-room space S2 to the in-bed air conditioner 102. Note that other operations of the air-conditioning controller 405 are the same as those of the air-conditioning controller 105 shown in FIG. 1.

As described above, in the present embodiment, the action schedule manager 441 that manages an action schedule of a person is referred to, and the in-bed air conditioner 102 is brought into operation a predetermined time period before a bedtime obtained from the action schedule to adjust the temperature of the in-bed space S1. It is thus possible to automatically adjust the temperature of the in-bed space S1 to a temperature suitable for sleep by the bedtime.

Sixth Embodiment

In the above-described first embodiment, the in-room air conditioner 103 including one outlet 103a is controlled. The present embodiment will describe an air-conditioning control system which controls an in-room air conditioner including two outlets.

Figure 8:
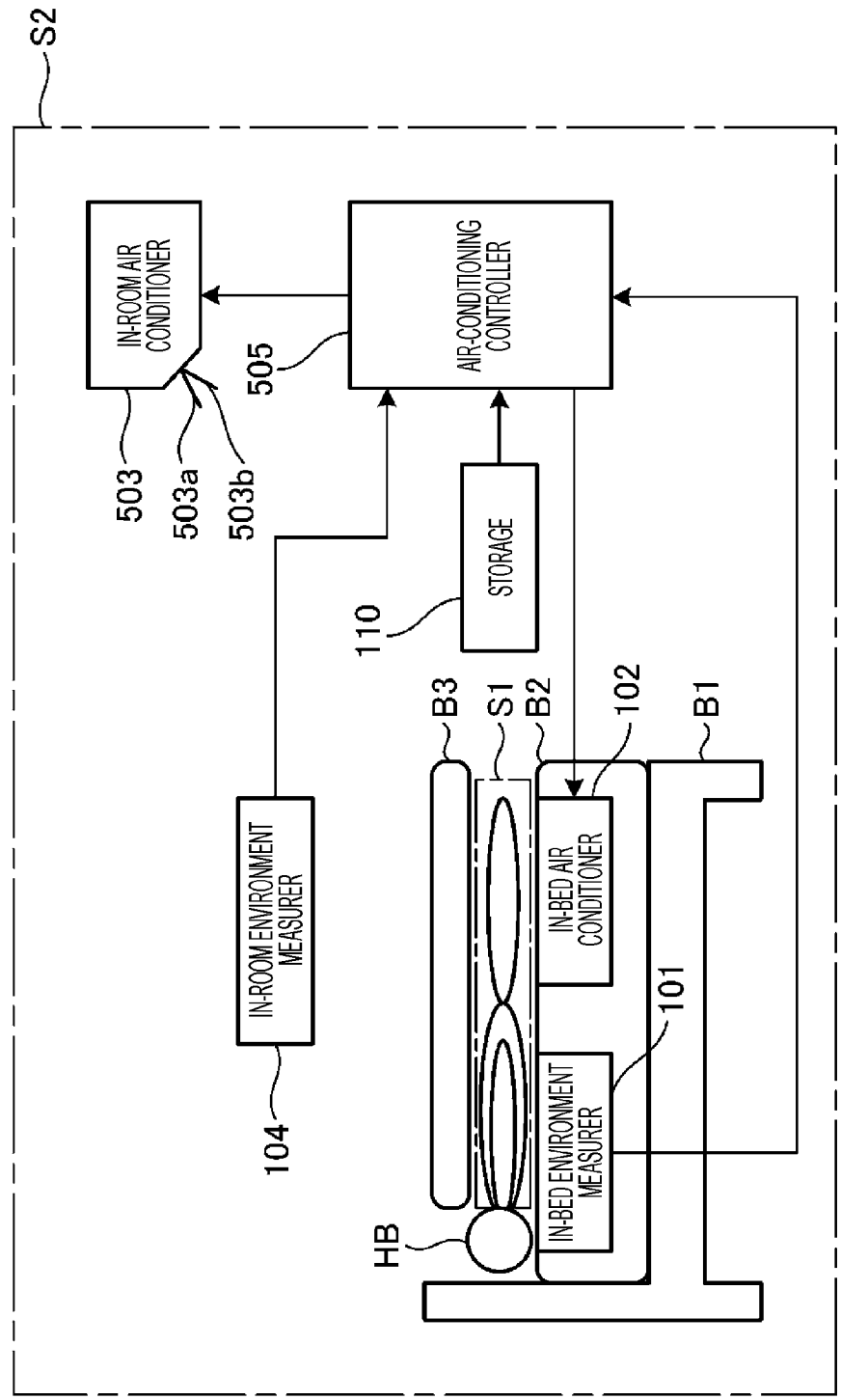
FIG. 8 is a diagram showing an example of the configuration of an air-conditioning control system according to a sixth embodiment of the present disclosure.

FIG. 8 is a diagram showing an example of the configuration of an air-conditioning control system according to a sixth embodiment of the present disclosure. The air-conditioning control system shown in FIG. 8 includes an in-bed environment measurer 101, an in-bed air conditioner 102, an in-room air conditioner 503, an in-room environment measurer 104, a storage 110, and an air-conditioning controller 505. Note that same components as those in FIG. 1 are denoted by same reference characters in FIG. 8 and that a detailed description thereof will be omitted.

The in-room air conditioner 503 is composed of, for example, an air conditioner or the like and is attached to an upper portion of one of walls forming an in-room space S2. The in-room air conditioner 503 can perform cooling operation, heating operation, and dehumidification operation and adjusts a temperature of the in-room space S2 in accordance with an operating state, a setup temperature, and the like. The in-room air conditioner 503 includes a first outlet (a first louver) 503a and a second outlet (a second louver) 503b and can set wind directions to two different directions. Note that the number of outlets (louvers) is not particularly limited to the above-described example and that three or more outlets may be used.

The air-conditioning controller 505 controls the wind direction of one of the first and second outlets 503a and 503b such that the wind direction is a bed direction (a direction in which the in-bed air conditioner 102 is located) at the time of operating the in-room air conditioner 503. For example, the air-conditioning controller 505 in summer puts the in-room air conditioner 503 to work and simultaneously sets one wind direction of the in-room air conditioner 503 to a downward direction by turning the second outlet 503b downward such that one airflow from the in-room air conditioner 503 arrives easily at the in-bed air conditioner 102. The air-conditioning controller 505 also sets the other wind direction of the in-room air conditioner 503 to an upward direction by turning the first outlet 503a upward and adjusts a temperature of the whole of the in-room space S2 with another airflow from the in-room air conditioner 503. Note that other operations of the air-conditioning controller 505 are the same as those of the air-conditioning controller 105 shown in FIG. 1.

As described above, in the present embodiment, the wind direction of one of the first and second outlets 503a and 503b of the in-room air conditioner 503 is controlled so as to be the bed direction. It is thus possible to efficiently supply temperature-adjusted air from the one outlet to the in-bed air conditioner 102 and efficiently supply temperature-adjusted air from the other outlet to the in-room space S2. This makes it possible to simultaneously make an in-bed space S1 and the in-room space S2 comfortable.

Seventh Embodiment

The above-described first embodiment has described an example in which the in-bed air conditioner 102 and the in-room air conditioner 103 are controlled in accordance with a difference between an in-bed temperature difference and an in-room temperature difference. The present embodiment will describe an air-conditioning control system which controls an in-bed air conditioner 102 and an in-room air conditioner 103 in accordance with relations between an in-bed temperature difference and a first threshold and between an in-room temperature difference and a second threshold.

Figure 9:
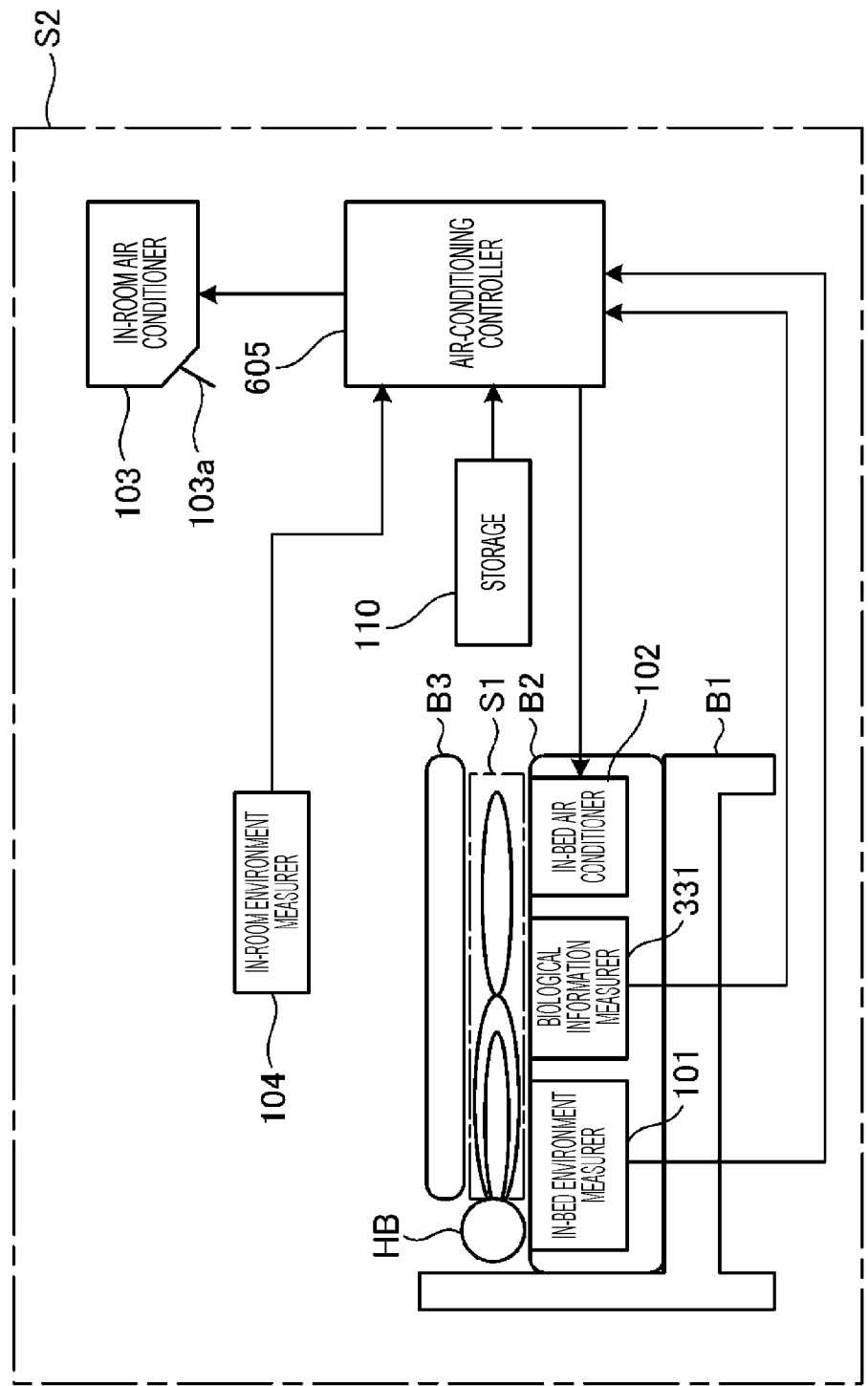
FIG. 9 is a diagram showing an example of the configuration of an air-conditioning control system according to a seventh embodiment of the present disclosure.

FIG. 9 is a diagram showing an example of the configuration of an air-conditioning control system according to a seventh embodiment of the present disclosure. The air-conditioning control system shown in FIG. 9 includes an in-bed environment measurer 101, the in-bed air conditioner 102, the in-room air conditioner 103, an in-room environment measurer 104, a storage 110, a biological information measurer 331, and an air-conditioning controller 605. Note that same components as those in FIGS. 1 and 6 are denoted by same reference characters in FIG. 9 and that a detailed description thereof will be omitted.

More specifically, the air-conditioning controller 605 judges whether the condition that the in-bed temperature difference is not less than the first threshold and the condition that the in-room temperature difference is not less than the second threshold are both met. This corresponds to judging whether the condition that a bed interior is uncomfortable and the condition that a room interior is uncomfortable are both met.

Additionally, the air-conditioning controller 605 acquires information on action of a person in the room interior from the biological information measurer 331. The air-conditioning controller 605 judges whether the acquired information on the action of the person indicates that the person is active. For example, the biological information measurer 331 includes a radio-frequency sensor which measures the amount of activity of a person, and the air-conditioning controller 605 judges whether the amount of activity obtained from the radio-frequency sensor is not less than a threshold. In addition, the air-conditioning controller 605 may judge whether heartbeat, respiration, or the like is measured at a bed or the like. This is because if the amount of activity is not less than the threshold and heartbeat or respiration is not measured at the bed, a person is often active.

For example, the biological information measurer 331 may include a wearable inertial sensor which measures the amount of activity, and the air-conditioning controller 605 may judge whether the amount of activity obtained from the inertial sensor is not less than a threshold. Additionally, the air-conditioning controller 605 may judge that a person is active if the measured degree of fluctuation in heartbeat is not more than a threshold.

Note that a method for acquiring information on action of a person in the room interior is not particularly limited to the above-described example. For example, information on action of a person in the room interior may be acquired from a terminal (for example, a smartphone) owned by the person instead of the biological information measurer 331. In this case, a sleep-related application may operate in the terminal owned by the person, and a notification that a sleep start operation is performed or information to be transmitted in the wake of a sleep start operation may be transmitted from the terminal to the air-conditioning controller 605 if the sleep start operation is performed in the application. The air-conditioning controller 605 judges presence or absence of reception of the information.

If the judgment as to whether the condition that the in-bed temperature difference is not less than the first threshold and the condition that the in-room temperature difference is not less than the second threshold are both met and the judgment as to whether information on action of a person indicates that the person is active are both affirmative, the air-conditioning controller 605 controls a wind direction of the in-room air conditioner 103 such that the wind direction is a direction for in-room air conditioning. This is to give priority to comfort of a person active in the room interior.

If the in-room temperature difference obtained after that is less than the second threshold, the air-conditioning controller 605 brings the in-bed air conditioner 102 into operation and sets the wind direction of the in-room air conditioner 103 to a bed direction. Since air in the room interior which is air to be fed into the bed interior is comfortable, the bed interior can be efficiently made comfortable.

Alternatively, if information on action of a person which is acquired after that indicates being about to sleep or being asleep, the air-conditioning controller 605 may bring the in-bed air conditioner 102 into operation and set the wind direction of the in-room air conditioner 103 to the bed direction. For example, the air-conditioning controller 605 judges whether heartbeat, respiration, or the like is measured at a bed or the like. For example, the air-conditioning controller 605 may judge presence or absence of reception of information transmitted from a sleep-related application as described above.

With the above-described configuration, even if the room interior is not comfortable, sleep of a person which is about to sleep or is asleep can be made comfortable by giving priority to in-bed air conditioning.

Eighth Embodiment

The present embodiment will describe an air-conditioning control system which controls a wind direction of an in-room air conditioner 103 on the basis of a relation between an in-bed temperature difference and an in-room temperature difference. Note that since the configuration of the air-conditioning control system according to the present embodiment is the same as that of the air-conditioning control system shown in FIG. 1, an illustration and a detailed description of the air-conditioning control system will be omitted, and that differences from the air-conditioning control system shown in FIG. 1 will be described in detail.

More specifically, an outlet 103a of the in-room air conditioner 103 is configured such that a ratio between a bed direction and a direction other than the bed direction in the wind direction is changeable. An air-conditioning controller 105 sets the ratio between the bed direction and the direction other than the bed direction in the wind direction of the in-room air conditioner 103 in accordance with a ratio between the in-bed temperature difference and the in-room temperature difference. For example, if the ratio between the in-bed temperature difference and the in-room temperature difference is 8:2, the air-conditioning controller 105 turns 80% of a wind opening of the in-room air conditioner 103 in the bed direction and turns 20% in the direction other than the bed direction.

With the above-described configuration, it is possible to preferentially air-condition one with a higher degree of discomfort of a bed interior and a room interior while air-conditioning the bed interior and the whole of the room interior. The other can thus be inhibited from falling into an uncomfortable state at the time of air-conditioning only one of the bed interior and the room interior.

Note that a ratio associated with the wind direction may be a temporal ratio associated with the wind direction instead of the ratio associated with the wind opening as described above. For example, if the ratio between the in-bed temperature difference and the in-room temperature difference is 8:2, the air-conditioning controller 105 sets the wind direction of the in-room air conditioner 103 to the bed direction for 80% of a predetermined time period and to the direction other than the bed direction for 20% of the predetermined time period.

Modification

A process or a configuration according to each embodiment may be incorporated into a process or a configuration according to one of the other embodiments. More specifically, the cooperation control according to the seventh embodiment may be executed in the cooperation control according to the third embodiment. For example, the in-bed air conditioner 102 and the in-room air conditioner 103 may be controlled in accordance with relations between an in-bed comfort level difference and a predetermined threshold and between an in-room comfort level difference and another predetermined threshold.

An air-conditioning control system according to an aspect of the present disclosure has an in-bed air conditioner which adjusts an in-bed temperature and performs collaborative control of an in-room air conditioner and the in-bed air conditioner. The air-conditioning control system is thus useful as a system for a bedroom which improves a sleep environment.

What is claimed is:

1. An air-conditioning control method for cooperatively controlling (i) an in-bed air conditioner which adjusts an in-bed temperature using air in a room interior and (ii) an in-room air conditioner which adjusts an in-room temperature, using a processor, the air-conditioning control method comprising:

acquiring the in-bed temperature from an in-bed environment measurer;

acquiring the in-room temperature from an in-room environment measurer; and performing cooperation control that controls operation of the in-bed air conditioner and a wind direction of the in-room air conditioner on the basis of the acquired in-bed temperature and the acquired in-room temperature, wherein the cooperation control includes:

calculating an in-bed temperature difference, which is a difference between the in-bed temperature and a target in-bed temperature;

calculating an in-room temperature difference, which is a difference between the in-room temperature and a target in-room temperature; and activating the in-bed air conditioner and setting the wind direction of the in-room air conditioner to a bed direction in response to the in-bed temperature difference being larger than the in-room temperature difference.

2. The air-conditioning control method according to claim 1, further comprising:

acquiring the target in-bed temperature and the target in-room temperature from a storage.

3. The air-conditioning control method according to claim 2, further comprising:

acquiring information on an action of a person in the room interior from a biological information measurer or a terminal owned by the person, wherein the cooperation control further includes a process that controls the operation of the in-bed air conditioner and the wind direction of the in-room air conditioner on the basis of a relation between the in-bed temperature difference and a first threshold, a relation between the in-room temperature difference and a second threshold, and the acquired information on the action of the person.

4. The air-conditioning control method according to claim 3, wherein
the process is performed by:
controlling the wind direction of the in-room air conditioner to a direction for in-room air conditioning, when the in-bed temperature difference is not less than the first threshold, the in-room temperature difference is not less than the second threshold, and the acquired information on the action of the person indicates that the person is active, and
activating the in-bed air conditioner and setting the wind direction of the in-room air conditioner to the bed direction when the information on the action of the person, which is acquired after the controlling of the wind direction of the in-room air conditioner to the direction for in-room air conditioning, indicates that the person is about to sleep or is asleep.

5. The air-conditioning control method according to claim 1, further comprising:
acquiring an in-bed humidity from the in-bed environment measurer;
acquiring an in-room humidity from the in-room environment measurer; and
acquiring a target in-bed comfort level and a target in-room comfort level from the storage, wherein
the cooperation control further includes:
calculating an in-bed comfort level which serves as a barometer for in-bed comfort using the in-bed temperature and the in-bed humidity and calculating an in-bed comfort level difference which is a difference between the in-bed comfort level and the target in-bed comfort level,
calculating an in-room comfort level which serves as a barometer for in-room comfort using the in-room temperature and the in-room humidity and calculating an in-room comfort level difference which is a difference between the in-room comfort level and the target in-room comfort level, and
controlling the operation of the in-bed air conditioner and the wind direction of the in-room air conditioner on the basis of the in-bed comfort level difference and the in-room comfort level difference.

6. The air-conditioning control method according to claim 1, further comprising:
acquiring biological information of a person from a biological information measurer; and
determining a sleep-related state of the person on the basis of the biological information, wherein
in the cooperation control, at least one of the operation of the in-bed air conditioner or a setup temperature of the in-room air conditioner is controlled on the basis of the in-bed temperature, the in-room temperature, and the sleep-related state.

7. The air-conditioning control method according to claim 6, wherein
in the cooperation control, the in-bed air conditioner is activated when it is determined that the sleep-related state is a sleeping state.

8. The air-conditioning control method according to claim 6, wherein
in the cooperation control, the in-bed air conditioner is activated when it is determined that the sleep-related state is a waking state.

9. The air-conditioning control method according to claim 6, wherein
when the sleep-related state shifts to a sleeping state in the cooperation control,
the setup temperature of the in-room air conditioner is raised with the in-bed air conditioner kept operating when the in-room air conditioner is in cooling or dehumidification operation, and
the in-bed air conditioner is brought out of operation and the setup temperature of the in-room air conditioner is lowered when the in-room air conditioner is in heating operation.

10. The air-conditioning control method according to claim 6, wherein
when the sleep-related state is a state having a light sleep before rising in the cooperation control,
the setup temperature of the in-room air conditioner is raised with the in-bed air conditioner kept operating when the in-room air conditioner is in cooling or dehumidification operation, and
the setup temperature of the in-room air conditioner is raised when the in-room air conditioner is in heating operation.

11. The air-conditioning control method according to claim 6, wherein
the biological information includes body motion data which represents motion of the person during sleep,
the determining of the sleep-related state includes determining the sleep-related state from the body motion data and the in-bed temperature, and
the setup temperature of the in-room air conditioner is lowered with the in-bed air conditioner kept activating when the sleep-related state is a state having difficulty in sleeping well in the cooperation control.

12. The air-conditioning control method according to claim 1, further comprising:
acquiring an action schedule from an action schedule manager which manages the action schedule of the person, wherein
in the cooperation control, the in-bed air conditioner is activated a predetermined time period before a bedtime indicated by the action schedule.

13. The air-conditioning control method according to claim 1, wherein
the in-room air conditioner has a first outlet and a second outlet, and
in the cooperation control, a wind direction of at least one of the first outlet or the second outlet is controlled to be directed to the bed direction.

14. An air-conditioning control method for cooperatively controlling (i) an in-bed air conditioner which adjusts an in-bed temperature using air in a room interior and (ii) an in-room air conditioner which adjusts an in-room temperature, using a processor, the air-conditioning control method comprising:
acquiring the in-bed temperature from an in-bed environment measurer;
acquiring the in-room temperature from an in-room environment measurer;
performing cooperation control that controls operation of the in-bed air conditioner and a wind direction of the in-room air conditioner on the basis of the acquired in-bed temperature and the acquired in-room temperature; and acquiring a target in-bed temperature and a target in-room temperature from a storage, wherein the cooperation control includes:

calculating an in-bed temperature difference, which is a difference between the in-bed temperature and the target in-bed temperature;

calculating an in-room temperature difference, which is a difference between the in-room temperature and the target in-room temperature;

controlling the operation of the in-bed air conditioner and the wind direction of the in-room air conditioner on the basis of the in-bed temperature difference and the in-room temperature difference; and setting a ratio between the bed direction and a direction other than the bed direction in the wind direction of the in-room air conditioner in accordance with a ratio between the in-bed temperature difference and the in-room temperature difference.

15. A, air-conditioning control method for cooperatively controlling (i) an in-bed air conditioner which adjusts an in-bed temperature using air in a room interior and (ii) an in-room air conditioner which adjusts an in-room temperature, using a processor, the air-conditioning control method comprising:

acquiring the in-bed temperature from an in-bed environment measurer;

acquiring the in-room temperature from an in-room environment measurer;

performing cooperation control that controls operation of the in-bed air conditioner and a wind direction of the in-room air conditioner on the basis of the acquired in-bed temperature and the acquired in-room temperature;

acquiring a target in-bed temperature and a target in-room temperature from a storage; and acquiring information on an action of a person in the room interior from a biological information measurer or a terminal owned by the person, wherein the cooperation control includes:

calculating an in-bed temperature difference, which is a difference between the in-bed temperature and the target in-bed temperature;

calculating an in-room temperature difference, which is a difference between the in-room temperature and the target in-room temperature;

controlling the wind direction of the in-room air conditioner to a direction for in-room air conditioning, when the in-bed temperature difference is not less than a first threshold, the in-room temperature difference is not less than a second threshold, and the acquired information on the action of the person indicates that the person is active, and activating the in-bed air conditioner and setting the wind direction of the in-room air conditioner to the bed direction, when the in-room temperature difference, which is acquired after the controlling of the wind direction of the in-room air conditioner to the direction for in-room air conditioning, is less than the second threshold.

16. An air-conditioning control method for cooperatively controlling (i) an in-bed air conditioner which adjusts an in-bed temperature using air in a room interior and (ii) an in-room air conditioner which adjusts an in-room temperature, using a processor, the air-conditioning control method comprising:

acquiring the in-bed temperature from an in-bed environment measurer;

acquiring the in-room temperature from an in-room environment measurer;

performing cooperation control that controls operation of the in-bed air conditioner and a wind direction of the in-room air conditioner on the basis of the acquired in-bed temperature and the acquired in-room temperature; and acquiring a target in-bed temperature from a storage, wherein the cooperation control includes:

activating the in-bed air conditioner and setting the wind direction of the in-room air conditioner to a bed direction in response to the in-room temperature being closer to the target in-bed temperature than the in-bed temperature.

17. An air-conditioning control system comprising:

an in-bed air conditioner which adjusts an in-bed temperature using air in a room interior;

an in-room air conditioner which adjusts an in-room temperature;

an in-bed environment measurer, including a temperature sensor which measures the in-bed temperature;

an in-room environment measurer, including a temperature sensor which measures the in-room temperature; and a controller, including a processor which performs cooperation control that controls operation of the in-bed air conditioner and a wind direction of the in-room air conditioner on the basis of the in-bed temperature acquired from the in-bed environment measurer and the in-room temperature acquired from the in-room environment measurer, wherein, in the cooperation control, the controller performs operations including:

calculating an in-bed temperature difference, which is a difference between the in-bed temperature and a target in-bed temperature;

calculating an in-room temperature difference, which is a difference between the in-room temperature and a target in-room temperature; and activating the in-bed air conditioner and setting the wind direction of the in-room air conditioner to a bed direction in response to the in-bed temperature difference being larger than the in-room temperature difference.

* * * * *